United States Patent [19]
Evans et al.

[11] Patent Number: 5,985,600
[45] Date of Patent: Nov. 16, 1999

[54] NUCLEIC ACID ENCODING DELTA OPIOID RECEPTOR

[75] Inventors: Christopher J. Evans, Venice; Duane E. Keith, Jr., Woodland Hills; Robert H. Edwards, Los Angeles, all of Calif.

[73] Assignee: The Regents of the University of California, Oakland, Calif.

[21] Appl. No.: 08/411,859

[22] Filed: Mar. 28, 1995

Related U.S. Application Data

[63] Continuation of application No. 07/929,200, Aug. 13, 1992, abandoned.

[51] Int. Cl.$^6$ ............... C12N 15/12; C07K 14/705
[52] U.S. Cl. ............... 435/69.1; 435/252.3; 435/325; 435/365; 435/254.2; 435/348; 435/320.1; 536/23.5
[58] Field of Search ............... 435/69.1, 240.2, 435/252.3, 254.11, 320.1, 325, 365, 254.2, 348; 536/23.5

[56] References Cited

PUBLICATIONS

Libert et al., Science, 244, 569–572, 1989.
Gramsch et al., "Monoclonal Anti–idiotypic Antibodies to Opioid Receptors," *Jour of Biological Chem*, vol. 263, No. 12, pp. 5853–5859 (1988).
Machida et al., "Three Technical Approaches for Cloning Opioid Receptors," *Natl Institute on Drug Abuse Research Monograph Series*, pp. 93–110, (1988).
Simonds et al., "Purification of the opiate receptor of NG108–15 neuroblastoma–glioma hybrid cells," *Proc. Natl. Acad. Sci.*, vol. 82, pp. 4974–4978 (1985).
Smith et al., "Problems and Approaches in Studying Membrane Opioid Receptors," *Natl Institute on Drug Abuse Research Monograph Series*, pp. 69–84, (1991).
Eberwine et al (1987) Fed. Proc. 46(4): 1444 (Abstr.#6582).
Evans et al (1992a) Soc. Neurosci: Abstr. 18(1): 21 (Abstr. #16.1).
Evans et al (1992b) Science 258: 1952–1955.
Xie et al (1992) Proc. Nat'l Acad Sci. 89: 4124–4128.
Yu et al (1986) J. Biol. Chem. 261(3): 1065–1090.
Carr et al (1989) Immunol. Lett. 20: 181–186.
Sanger et al (1977) Proc. Nat'Acad Sci. 74(12): 5463–5467.
Davis et al (1986) "Basic Methods in Molecular Biology", Elsevier Science Publishing Co., Inc. New York., pp. 1–372. (Table of Contents provided).
Kieffer et al (1992) Proc. Nat'l Acad Sci. 89: 12048–12052.
Bochet et al., *Molecular Pharmacology* (1988) 34: 436–443.
Law et al., *Molecular Pharmacology* (1982) 21 :438–91.
Schofield et al., *The EMBO Journal* (1989) 8(2):489–495.
Xie et al., *Proc. Natl. Acad. Sci.* (1992) 89:4124–4128.

*Primary Examiner*—Sally P. Teng
*Attorney, Agent, or Firm*—MorrisonFoersterLLP

[57] ABSTRACT

Nucleic acid molecules comprising a nucleotide sequence encoding a mammalian delta opioid receptor are disclosed. The invention provides recombinant materials for the production of mammalian delta opioid receptors.

12 Claims, 8 Drawing Sheets

```
GCACGGTGGAGACGGACACGGCGGCCATG GAG CTG GTG CCC TCT GCC CGT GCG GAG CTG CAG TCC TCG CCC CTC
                              Met Glu Leu Val Pro Ser Ala Arg Ala Glu Leu Gln Ser Ser Pro Leu
GTC AAC*CTC TCG GAC GCC TTT CCC AGC GCC TTC CCC AGC GCC GCC AAT GCG TCG GGG TCG CCG GGA
Val Asn*Leu Ser Asp Ala Phe Pro Ser Ala Phe Pro Ser Ala Gly Ala Asn*Ala Ser Gly Ser Pro Gly
GCC CGT AGT GCC TCG TCC CTC GCC CTA GCC ATC GCC ACC GCG CTC TAC TCG GCT GTG TGC GCA GTG
Ala Arg Ser Ala Ser Ser Leu Ala Leu Ala Ile Ala Thr Ala Leu Tyr Ser Ala Val Cys Ala Val
GGG CTT CTG GGC AAC GTG CTC GTG CTG ATG TTT GGC ATC GTC CGG. TAC ACC TTG AAG ACC AAC AAC
Gly Leu Leu Gly Asn Val Leu Val Leu Met Phe Gly Ile Val Arg Tyr Thr Leu Lys Thr Ala Asn
ATC TAC ATC TTC AAT CTG GCT TTG GCT GAT GCG GCA CTG GCC ACG CTG ACG CTG ACG CTC CTC CCC TTC ATT GAC TAC TGC AAG
Ile Tyr Ile Phe Asn Leu Ala Leu Ala Asp Ala Leu Ala Thr Ser Thr Leu Pro Phe Gln Ser Ile Asp Tyr Tyr Asn
TAC TTG ATG GAA ACG TGG CCG TTT GGC GAG CTG CTG TGC AAG GCT GTG CTC TCC ATT GCT GTC TGC CAT CCT GTC
Tyr Leu Met Glu Thr Trp Pro Phe Gly Glu Leu Leu Cys Lys Ala Val Leu Ser Ile Ala Val Cys His Pro Val
ATG TTC ACT AGC ATC TTC ACC CTC ACC ATG ATG AGC GTG GAC CGC TAC ATA AAT ATC TGC ATC TGG TTG GCT TCA
Met Phe Thr Ser Ile Phe Thr Leu Thr Met Met Ser Val Asp Arg Tyr Ile Asn Ile Cys Ile Trp Leu Ala Ser
AAA GCC CTG GAC TTC CGG ACA CCA GCC AAG GCC AAG CTG ATC AAT ATC TGC ATC TGG TTG GCT TCA
Lys Ala Leu Asp Phe Arg Thr Pro Ala Lys Ala Lys Leu Ile Asn Ile Cys Ile Trp Leu Ala Ser
GGT GTG GGG GTC CCC ATC ATG GTC ATG GCA GTG ACC CAA CCC CGG GAT GGT GCA GTG GTA TGC ATG CTC
Gly Val Gly Val Pro Ile Met Val Met Ala Val Thr Gln Pro Arg Asp Gly Ala Val Val Cys Met Leu
```

FIG.5a

CAG TTC CCC AGT CCC TGG TAC TGG GAC ACT GTG ACC AAG ATC TGC GTG TTC CTC TTT GCC TTC GTG
Gln Phe Pro Ser Pro Trp Tyr Trp Asp Thr Val Thr Lys Ile Cys Val Phe Leu Phe Ala Phe Val

GTG CCG ATC CTC ATC ATC ACG ATC GTG TGC TAT GGC CTC ATG CTA CTG CGC AGC GTG CGT CTG CTG
Val Pro Ile Leu Ile Ile Thr Ile Val Cys Tyr Gly Leu Met Leu Leu Arg Ser Val Arg Leu Leu

TCC GGT TCC AAG GAG AAG GAC CGC AGC CGG CGC ATG ACG CGC ATG GTG CTG GTG GTG GGC GCC
Ser Gly Ser Lys Glu Lys Asp Arg Ser Arg Arg Arg Met Thr Arg Met Val Leu Val Val Gly Ala

TTC GTG GTG TGC TGG GCG CCC ATC CAC ATC TTC GTC ATC GTC TGG ACG CTG GTG GAC ATC AAT CGG CGC
Phe Val Val Cys Trp Ala Pro Ile His Ile Phe Val Ile Val Trp Thr Leu Val Asp Ile Asn Arg Arg

GAC CCA CTT GTG GTG GCC GCA CTG CAC CTG TGC ATT GCG CTG GGC TAC GCC AAC AGC CTC AAC CCG
Asp Pro Leu Val Val Ala Ala Leu His Leu Cys Ile Ala Leu Gly Tyr Ala Asn Ser Leu Asn Pro

GTT CTC TAC GCC TTC CTG GAC GAG AAC TTC AAG CGC TGC TTC CGC CAG CTC TGT CGC ACG CCC TGC GGC
Val Leu Tyr Ala Phe Leu Asp Glu Asn Phe Lys Arg Cys Phe Arg Gln Leu Cys Arg Thr Pro Cys Gly

CGC CAA GAA CCC GGC AGT CTC CGT CCC CGC CAG GCC ACC ACG CGT GAG CGT GTC ACT GCC TGC ACC
Arg Gln Glu Pro Gly Ser Leu Arg Arg Pro Arg Gln Ala Thr Thr Arg Glu Arg Val Thr Ala Cys Thr

CCC TCC GAC GGC CCG GGT GGC GCT GCC GCC TGA CCTACCCGACCTTCCCCTTAAACGCCCCTCCCCAAGTGAAGTGA
Pro Ser Asp Gly Pro Gly Gly Gly Ala Ala Ala ***

CAGAGGCCACACCGAGCTCCCTGGGGAGGCTGTGGCCACCAGGACAGCTAGAATTGGGCCTGCACAGAGGGGAGGCTCCTGTGGGGAC
GGCCTGAGGGACAGAGGGGATCAAAGGCTCCAGTTGGAACGGTTGGAACAGAGCTGGTGATTCCTAAGTCCATTAGTAAGGCCTCT
AATGGGACAGAGGGCTCGCCTGAGATAACATCGGGTTGGCTGGCCCTTTTGAACACCCAGTCCAAGACCCAAGGATTCCAGCTCCA
AACCAGGAGACAGGGGCAGTCATTGGGCTGATGATTCAGGCAAGCCTGGAGAGCCCAGCATTTGTGTTATGGGGAGGATCTCTAGAGAAG
AAGGGGACAGGGGAAGAGGGTCAAAGTTCTCACCACCTTTCTAACTACTCAGTTGGTTCAGGAGATAAGCTGTTGAGGGCTAGGGCAACGTGACTTCTCTGTAGAGAG
ACGTTGGAGAGCCGGGCCTGATGTGGGGCAGGCTGGAGGCTGAGGCTGGAAAATTAAGGACCAACAGCCCGG
TACAAGCCGGGCCTGATGTGGGGCAGGCTGGAGGCTGAGGCTGGAAAATTAAGGACCAACAGCCCGG

FIG.5b

```
            *20              *      40
MELVPSARAELQSSPLVNLSDAFPSAFPSAGANASGSPGARSAS--SLALAIAITALYSA
      MELTSEQFNGSQVWIPSPFDLNGSLGPSNGSNQTEPYYDMTSNAVLTFIYFV 60              80              100
VCAVGLLGNVLVMFGIVRYTKLKTATNIYIFNLALADALATSTLPFQSAKYLMETWPFGE
VCVVGLCGNTLVIYVILRYAKMKTITNIYILNLAIADELFMLGLPFLAMQVALVHWPFGK 120             140             160
LLCKAVLSIDYYNMFTSIFTLTMMSVDRYIAVCHPVKALDFRTPAKAKLINICIWVLASG
AICRVVMTVDGINQFTSIFCLTVMSIDRYLAVVHPIKSAKWRRPRTAKMINVAVWGVSLI 180             200             220
VGVPIMVMAVTQPRD-GAVVCMLQFPSPSWYWDTVTKICVFLFAFVVPILIITVCYGLML
VILPIMIYAGLRSNQWGRSSCTINWPGESGAWYTGFIIYAFILGFLVPLTIICLCYLFII 240             260             280
LRLRSVRLLSGSKEKDRSLRRITRMVLVVVGAFVVCWAPIHIFVIVWTLVDINRRDPLVV
IKVKSSGIRVGSSKRKKSEKKVTRMVSIVVAVFIFCWLPFYIFNVSSVSVAIS-PTPALK 300             320             340
AALHLCIALGYANSSLNPVLYAFLDENFKRCFRQ-LCRTPCGRQEPGSLRRPRQATTRER
GMFDFVVILTYANSCANPILYAFLSDNFKKSFQNVLCLVKVSGAEDGERSDKQDKSRLN 360     370
VTACTPSDGPGGGAAA

ETTETQRTLLNGDLQTSI
```

FIG.6

NUCLEIC ACID ENCODING DELTA OPIOID RECEPTOR

This application is a continuation of application Ser. No. 07/929,200, filed Aug. 13, 1992, now abandoned.

This invention was made with Government support under Grant No. DA05010 awarded by the Alcohol, Drug Abuse and Mental Health Administration. The Government has certain rights in the invention.

TECHNICAL FIELD

The invention relates to substances involved in vertebrate nervous systems, and in particular to the delta opioid receptor and activities mediated thereby. Accordingly, the invention concerns recombinant materials useful for the production of delta opioid receptor, the receptor as a diagnostic tool, therapeutic and diagnostic compositions relevant to the receptor, and methods of using the receptor to screen for drugs that modulate the activity of the receptor.

BACKGROUND ART

The term "opioid" generically refers to all drugs, natural and synthetic, that have morphine-like actions. Formerly, the term "opiate" was used to designate drugs derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources have continued to use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

A significant feature of the analgesia produced by opioids is that it occurs without loss of consciousness. When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

The development of tolerance and physical dependence with repeated use is a characteristic feature of all opioid drugs, and the possibility of developing psychological dependence on the effect of these drugs is a major limitation for their clinical use. There is evidence that phosphorylation may be associated with tolerance in selected cell populations. (Louie, A. et al. *Biochem. Biophys. Res. Comm.,* 152: 1369–75 (1988)).

Acute opioid poisoning may result from clinical overdosage, accidental overdosage, or attempted suicide. In a clinical setting, the triad of coma, pinpoint pupils, and depressed respiration suggest opioid poisoning. Mixed poisonings including agents such as barbiturates or alcohol may also contribute to the clinical picture of acute opioid poisoning. In any scenario of opioid poisoning, treatment must be administered promptly.

The opioids interact with what appear to be several closely related receptors. Various inferences have been drawn from data that have attempted to correlate pharmacologic effects with the interactions of opioids with a particular constellation of opioid receptors. (Goodman and Gilman's, The Pharmacological Basis of Therapeutics, 7th ed 493–95 (MacMillan 1985)). For example, analgesia has been associated with mu and kappa receptors. Delta receptors are believed to be involved in alterations of affective behavior; this belief is based primarily on the localization of these receptors in limbic regions of the brain. Additionally, activation, e.g., ligand binding with stimulation of further receptor-mediated response, of delta opioid receptors is believed to inhibit the release of other neurotransmitters. The paths containing relatively high populations of delta opioid receptor are similar to the paths implicated to be involved in Huntington's disease. Accordingly, it is postulated that Huntington's disease may correlate with some effect on delta opioid receptors.

Pharmacologically, it has been found that there are two distinct classes of opioid molecules that can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., *Science* 179:1011–1014 (1973)), the differential pharmacological and physiological effects of both opioid peptide analogues and alkaloid opiates served to delineate multiple opioid receptors. Accordingly, three anatomically and pharmacologically distinct opioid receptor types have been described: delta, kappa and mu. Furthermore, each type is believed to have subtypes. (Wollemann, M., *J. Neurochem.,* 54(4):1095–1101 (1990); Lord, J. A., et al., *Nature,* 267:495–499, (1977)).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: *Biological Basis of Substance Abuse,* S. G. Korenman & J. D. Barchas, eds., Oxford University Press (in press); North, A. R., et al., *Proc. Natl. Acad. Sci. USA,* 87(18): 7025–29 (1990); Gross, R. A., et al., *Proc. Natl. Acad. Sci. U S A,* 87(18): 7025–29 (1990); Sharma, S. K., et al., *Proc. Natl. Acad. Sci. U.S.A.,* 72:(8) 3092–96 (1975)). Although the functional mechanisms are the same, the behavioral manifestations of receptor-selective drugs differ greatly. (Gilbert, P. E. & Martin, W. R., *J. Pharmacol. Exp. Ther.,* 198(1):66–82 (1976)). Such differences may be attributable in-part to the anatomical location of the different receptors.

Delta opioid receptors are of particular relevance for the present invention. Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex. (Mansour, A., et al., *Trends in Neurosci.,* 11(7): 308–14 (1988)). The rat cerebellum is remarkably devoid of opioid receptors including delta opioid receptors.

Several opioid molecules are known to selectively or preferentially bind delta receptors. Of the vertebrate endogenous opioids, the enkephalins, particularly met-enkephalin and leu-enkephalin, appear to possess the highest affinity for delta receptors, although the enkephalins also have high affinity for mu receptors. Additionally, the deltorphans, peptides isolated from frog skin, comprise a family of opioid peptides that have high affinity and selectivity for delta receptors. (Erspamer, V., et al., *Proc. Natl. Acad. Sci. USA*, 86(13): 5188–92 (1989)).

A number of synthetic enkephalin analogues are also delta-selective including:

(D-Ser$^2$) leucine enkephalin Thr (DSLET) (Garcel, G., et al., *F.E.B.S. Letters* 118(2): 245–247 (1980)); and (D-Pen$^2$, D-Pen$^5$) enkephalin (DPDPE) (Akiyama, K., et al., *P.N.A.S.* 82: 2543–2547 (1985))

Recently a number of other selective delta ligands have been synthesized, and their bioactivities and binding characteristics suggest the existence of more than one delta receptor subtype. (Takemori, A. E., et al., *Annual Review of Pharmacology and Toxicology*, 32:239–69 (1992); Negri, L., et al., *Eur. J. Pharmacol.*, 196:355–335 (1991); Sofuoglu, M., et al., *Pharmacologist* 32:151 (1990)).

The synthetic pentapeptide 2dAla, 5dLeu enkephalin (DADLE) was considered to be delta-selective; although DADLE shows high affinity for delta receptors, it also binds equally well to mu receptors. The synthetic peptide D-Ala$^2$, N-Me-Phe$^4$, Gly-ol$^5$-enkephalin (DAGO) has been found to be a selective ligand for mu-receptors.

The existence of multiple delta opioid receptors has been implied not only from the pharmacological studies addressed above, but also from molecular weight estimates obtained by use of irreversible affinity ligands. These studies indicate molecular weights for the delta opioid receptor that range from 30,000–60,000 daltons. (Evans, C. J., In: *Biological Basis of Substance Abuse*, S. G. Korenman & J. D. Barchas, Eds., Oxford University Press (in press); Bochet, P., et al., *Mol. Pharmacol.*, 34(4):436–43 (1988)). The various receptor sizes may represent alternative splice products, although this has not been established.

Many studies of the delta opioid receptor have been performed with the neuroblastoma/glioma cell line NG108-15. The NG108-15 cell line was generated by fusion of the rat glial cell line (C6BU-1) and the mouse neuroblastoma cell line (N18-TG2) (Klee, W. A. and Nirenberg, M. A., *P.N.A.S. USA* 71(9): 3474–3477 (1974)). The rat glial cell line expresses essentially no delta opioid receptors, whereas the mouse neuroblastoma cell line expresses low amounts of the receptor. Thus, a mouse chromosomal origin of the delta opioid receptors in the NG108-15 cells has been suggested. (Law, *Mol. Pharm.*, 21: 438–91).

Each NG108-15 cell is estimated to express approximately 300,000 delta-receptors. Only delta-type opioid receptors are expressed, although it is not known whether these represent more than a single subtype.

Thus, the NG108-15 cell line has served to provide considerable insight into the binding characterization of opioid receptors, particularly delta opioid receptors. However, the NG108-15 cell line is a cancer-hybrid, and it may not be completely representative of the delta receptor in endogenous neurons due to the unique cellular environment in the hybrid cells.

An extensive literature has argued that the opioid receptors are coupled to G-proteins (see, e.g., Schofield, P. R., et al., *Embo J.*, 8(2):489–95 (1989)), and are thus members of the family of G-protein coupled receptors. G-proteins are guanine nucleotide binding proteins that couple the extracellular signals received by cell surface receptors to various intracellular second messenger systems. Identified members of the G-protein-coupled family share a number of structural features, the most highly conserved being seven apparent membrane-spanning regions, which are highly homologous among the members of this family. (Strosberg, A. D., *Eur. J. Biochem.* 196(1):1–10 (1991)). Evidence that the opioid receptors are members of this family includes the stimulation of GTPase activity by opioids, the observation that GTP analogues dramatically effect opioid and opiate agonist binding, and the observation that pertussis toxin (which by ADP ribosylation selectively inactivates both the Gi and Go subfamilies of G-proteins) blocks opioid receptor coupling to adenylate cyclase and to K$^+$ and Ca$^{2+}$ channels. (Evans, C. J., In: *Biological Basis of Substance Abuse*, S. G. Korenman & J. D. Barchas, Eds., Oxford University Press (in press)).

The members of the G-protein-coupled receptor family exhibit a range of characteristics. Many of the G-protein-coupled receptors, e.g., the somatostatin receptor and the angiotensin receptor, have a single exon that encodes the entire protein coding region (Strosberg, A. D., *Eur. J. Biochem.* 196(1):1–10 (1991); Langord, K., et al., *B.B.R.C.* 138(3): 1025–1032 (1992)). However, others, such as substance-P receptor and the Dopamine D2 receptor contain the protein coding region. The D2 receptor is particularly interesting in that alternate splicing of the message gene gives rise to different transcribed products (i.e., receptors). (Evans, C. J., In: *Biological Basis of Substance Abuse*, S. G. Korenman & J. D. Barchas, Eds., Oxford University Press (in press); Strosberg, A. D., *Eur. J. Biochem.* 196(1):1–10 (1991)). Interestingly, somatostatin ligands are reported to bind to opioid receptors (Terenius, L., *Eur. J. Pharmacol.* 38: 211 (1976); Mulder, A. H., et al., *Eur. J. Pharmacol.* 205:1–6 (1991)) and, furthermore, to have similar molecular mechanisms. (Tsunoo, A., et al., *P.N.A.S.* 83: 9832–9836 (1986)).

In previous efforts to describe and purify opioid receptors two clones have been described that were hypothesized either to encode opioid receptors or a portion thereof. The first clone, which encodes opiate binding protein OBCAM (Schofield, P. R., et al., *Embo J.*, 8(2):489–95 (1989)) was obtained by utilizing a probe designed from an amino acid sequence contained in protein purified on a morphine affinity column. OBCAM does not have membrane spanning domains; however, it has a C-terminal domain that is characteristic of attachment of the protein to the membrane by a phosphatidylinositol linkage. This feature, which is shared by members of the immunoglobulin superfamily, is not common to the family of receptors coupled to G-proteins. Thus, it has been proposed that OBCAM is part of a receptor complex along with other components that are coupled to G-proteins. (Schofield, P. R., et al., *Embo J.*, 8(2):489–95 (1989)). At present, however, there is no direct evidence for such a complex.

A second proposed opioid receptor clone was obtained in an effort to clone a receptor that binds kappa opioid receptor ligands. (Xie, G. X., *Proc. Natl. Acad. Sci. USA*, 89: 4124–4128 (1992)). A DNA encoding a G-coupled receptor from a placental cDNA library was isolated. This receptor has an extremely high homology with the neurokinin B receptor (84% identical throughout the proposed protein sequence). When this clone was expressed in COS cells, it displayed opioid peptide displaceable binding of $^3$H-Bremazocine (an opiate ligand with high affinity for kappa receptors). However, the low affinity of this receptor for $^3$H-Bremazocine, and the lack of appropriate selectivity since this receptor binds both mu and delta ligands, makes it doubtful that this cloned molecule is actually an opioid receptor. Furthermore, characterization of opioid receptor proteins has proven difficult because of the instability of these membrane-bound receptors after they are solubilized, and purified delta opioid receptors have not been isolated. The previous reports estimating the molecular weights for opioid receptor proteins in the wide range from 30,000–60,000 daltons reflect the difficulty in isolating and characterizing this protein.

DISCLOSURE OF THE INVENTION

The invention provides recombinant materials and methods to produce mammalian delta opioid receptor. Methods for isolating the receptor, isolating the gene that encodes the receptor, recombinantly producing the receptor, and methods for using the receptor to screen for drugs that modulate the activity of the receptor are also provided.

Thus, in one aspect, the invention is directed to recombinant materials and methods for the production of a mammalian delta opioid receptor protein. Such materials and methods include isolated and purified forms or recombinantly produced forms of DNA encoding said delta opioid receptor protein, expression systems suitable for the production of the protein, and cells transformed with said expression systems. Especially useful are mammalian cells which express the gene in such a way that the delta opioid receptor protein is displayed at the surface of the cells. The cells of this type are especially useful products of the invention, since they offer means to screen native and synthetic candidate agonists and antagonists from the ligands which bind delta opioid receptors.

In still other aspects, the invention is directed to methods to screen candidate agonists and/or antagonists for ligands that activate the delta opioid receptors using the recombinant transformed cells of the invention. Such assays include binding assays using competition with ligands known to bind delta opioid receptors; agonist assays which analyze the transformed cells for activation of the secondary pathways associated with opioid receptor activation; and assays which evaluate the effect on binding of the candidate to the receptor by the presence or absence of sodium ion and GTP. Antagonist assays include the combination of the ability of the candidate to bind the receptor while failing to effect further activation, and, more importantly, competition with a known agonist. Still another aspect of the invention is provision of antibody compositions which are immunoreactive with the delta opioid receptor protein. Such antibodies are useful, for example, in purification of the receptors after solubilization or after recombinant production thereof.

In still other aspects, the invention is directed to probes useful for the identification of DNA which encodes related opioid receptors in various species or of different types and subtypes.

Accordingly, an object of the present invention is to provide an isolated and purified form of a DNA sequence encoding a delta opioid receptor.

Another object is to provide a recombinantly produced DNA sequence encoding a delta opioid receptor.

Another object is to produce an antisense sequence corresponding to known sense sequence encoding the delta opioid receptor.

Another object of the invention is to provide a DNA construct comprised of a control sequence operatively linked to a DNA sequence which encodes a delta opioid receptor and to provide recombinant host cells transformed with the DNA construct.

Another object is to isolate, clone and characterize, from various vertebrate species, DNA sequences encoding the various related receptors, by hybridization of the DNA derived from such species with a native DNA sequence encoding the delta opioid receptors of the invention.

An advantage of the present invention is that delta opioid receptor encoding DNA sequences can be expressed at the surface of host cells which can conveniently be used to screen drugs for their ability to interact with and/or bind to the receptors.

These and other objects, advantages and features of the present invention will become apparent to those persons skilled in the art.

BRIEF DESCRIPTION OF THE DRAWINGS

FIG. 5 is the DNA sequence encoding the DOR-1 delta opioid receptor, and the corresponding amino acid sequence of said delta opioid receptor (SEQ ID NO: 1 and SEQ ID NO: 2).

FIG. 6 depicts the deduced protein sequence of DOR-1, compared with the rat somatostatin receptor (SEQ ID NO: 2 and SEQ ID NO: 3). Consensus glycosylation sites predicted to fall in extracellular domains are indicated by an asterisk. Potential protein kinase C sites are listed in example 5. The seven predicted membrane spanning regions are underlined. These seven regions are predicted based on the hydrophobicity profile and published predictions (MacVector software program (IBI); T. Hopp, and K. Woods, *Proc. Natl. Acad. Sci.* USA 78, 3842–3828 (1981)). For sequencing, the cDNA insert was subcloned into pBluescript (Strategene), and both strands were sequenced from single-stranded DNA using Sequenase and Taq cycle sequencing (USB). For ambiguities due to compressions 7-deaza-dGTP replaced dGTP in the sequencing reactions and the products were resolved on formamide gels.

MODES OF CARRYING OUT THE INVENTION

Figure 1:
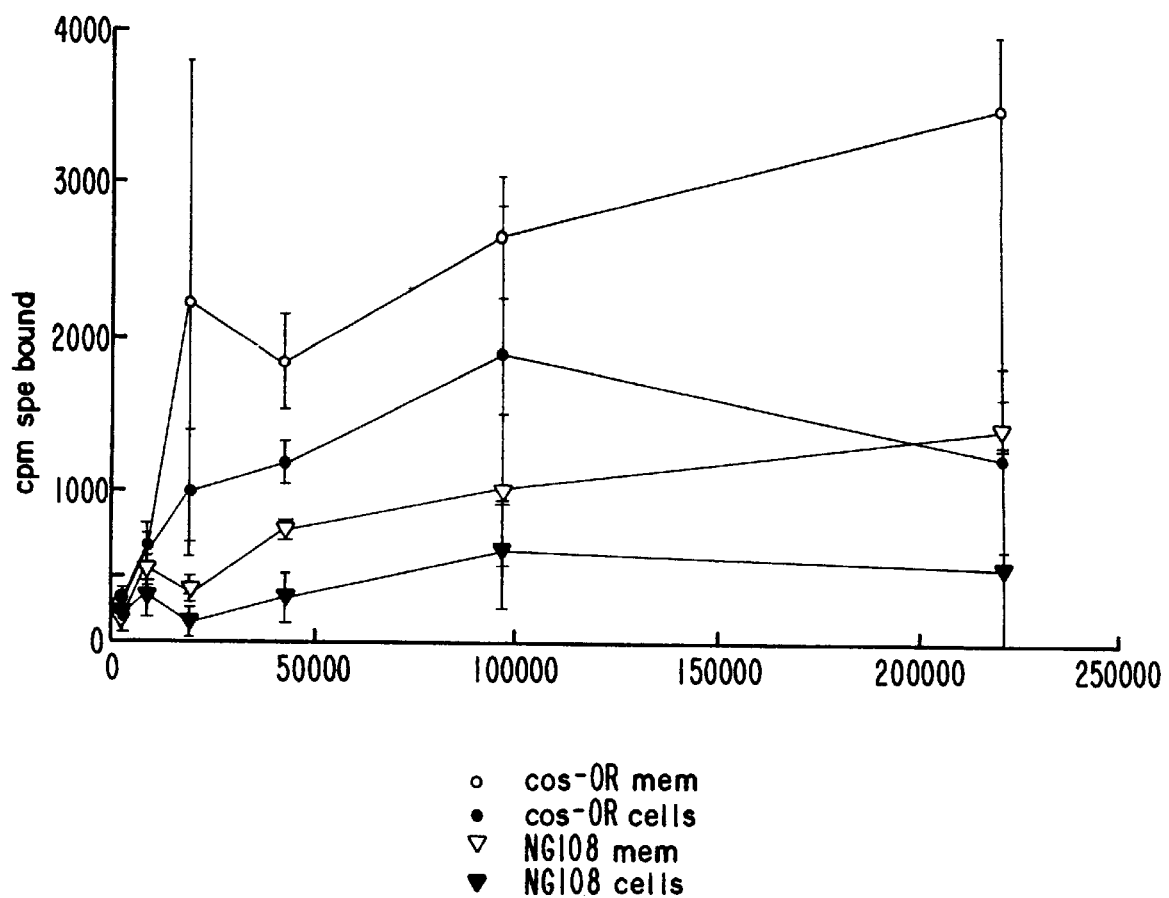
FIG. 1 depicts a comparison between $^3$H-Diprenorphine saturation curve of NG108-15 cells and COS cells three days following electroporation with DOR-1 in the CDM8 vector. Specific opioid binding was undetectable in nontransfected COS cells or COS cells transfected with plasmid alone.

The invention provides DNA encoding mammalian delta opioid receptor protein and additional recombinant materials and methods useful for the production of this protein. In addition, eucaryotic cells, such as COS cells, transformed with the recombinant materials of the invention so as to express delta opioid receptor protein at their surface are useful in screening assays to identify candidate opioid agonists and antagonists. In addition, antibodies may be raised to the recombinantly produced delta opioid receptor protein. These antibodies are useful in immunoassays for said protein and in affinity purification thereof.

Recombinant Delta Opioid Receptor

Illustrated hereinbelow is the obtention of a cDNA encoding murine delta opioid receptor. The complete DNA sequence of the cDNA, and the amino acid sequence encoded thereby are set forth herein in FIG. 5. The availability of this cDNA permits the retrieval of the corresponding delta opioid receptors-encoding DNA from other vertebrate species. Accordingly, the present invention places within the possession of the art, recombinant materials and methods for the production of cells expressing delta opioid receptors of various subtypes and of various vertebrate species. Thus, the cDNA of FIG. 5, or a portion thereof, may be used as a probe to identify that portion of vertebrate genomic DNA which encodes the corresponding delta opioid receptor protein. Sample methods as used to prepare the relevant genomic library and identify the delta opioid receptor-encoding gene are described for convenience hereinbelow.

In the alternative, the DNA of FIG. 5 or a portion thereof may be used to identify specific tissues or cells which express delta opioid receptor protein by analyzing the messenger RNA, for example, using Northern blot techniques. Those tissues which are identified as containing mRNA encoding delta opioid receptor protein using the probes of the invention are then suitable sources for preparation of cDNA libraries which may further be probed using the cDNA described hereinbelow.

The DNA encoding the various vertebrate delta opioid receptor proteins, obtained in general as set forth above, according to the standard techniques described hereinbelow, can be used to produce cells which express the delta opioid receptor at their surface; such cells are typically eucaryotic cells, in particular, mammalian cells such as COS cells or CHO cells. Suitable expression systems in eucaryotic cells for such production are described hereinbelow. The delta opioid receptor proteins may also be produced in procaryotes or in alternative eucaryotic expression systems for production of the protein per se. The protein may be ligated into expression vectors preceded by signal sequences to effect its secretion, or may be produced intracellularly, as well as at the cell surface, depending on the choice of expression system and host. If desired, the delta opioid receptor protein thus recombinantly produced may be purified using suitable means of protein purification, and, in particular, antibodies or fragments thereof immunospecific for the delta opioid receptor protein.

Screening for Opioid Agonists and Antagonists Using Recombinant Cells

The ability of a candidate compound to behave as an opioid agonist or antagonist may be assessed using the recombinant cells of the invention in a variety of ways. To exhibit either agonist or antagonist activity, the candidate compound must bind to the opioid receptor. Thus, to assess the ability of the candidate to bind, either a direct or indirect binding assay may be used. For a direct binding assay, the candidate binding compound is itself labeled, such as with a radioisotope or fluorescent label, and binding to the recombinant cells of the invention is assessed by comparing the acquisition of label by the recombinant cells to the acquisition of label by untransformed corresponding cells.

More convenient, however, is the use of a competitive assay wherein the candidate compound competes for binding to the recombinant cells of the invention with a labeled form of an opioid ligand known to bind to the receptor. Such ligands are themselves labeled using radioisotopes or fluorescent moieties, for example. A particularly suitable opioid known to bind to this receptor is diprenorphine. A typical protocol for such an assay is as follows:

In general, about $10^6$ recombinant cells are incubated in suspension in 1.0 ml of Kreb's Ringer Hepes Buffer (KRHB) at pH 7.4, 37° C. for 20 min with $^3$H-diprenorphine. Nonspecific binding is determined by the addition of 400 nM diprenorphine in the binding mixtures. Various concentrations of candidate compounds are added to the reaction mixtures. The incubations are terminated by collecting the cells on Whatman GF-B filters, with removal of excess radioactivity by washing the filters three times with 5 ml of KRHB at 0° C. After incubating at 20° C. overnight in 5 ml of Liquiscint (National Diagnostics, Somerville, N.J.), the radioactivity on the filters is determined by liquid scintillation counting.

The $K_d$ (dissociation constant) values for the candidate opiate ligands can be determined from the $IC_{50}$ value. (i.e., the concentration of ligand that results in a 50% decrease in binding of labeled diprenorphine).

The effects of sodium and GTP on the binding of ligands to the recombinantly expressed receptors can be used to distinguish agonist from antagonist activities. If the binding of a candidate compound is sensitive to $Na^+$ and GTP, it is more likely to be an agonist than an antagonist, since the functional coupling of delta opioid receptors to second messenger molecules such as adenylate cyclase requires the presence of both sodium and GTP. (Blume, et al., *P.N.A.S. U.S.A.*, 23: 26–35 (1979)). Furthermore, sodium, GTP, and GTP analogues have been shown to effect the binding of opioids and opioid agonists to opioid receptors. (Blume, *Life Sciences*, 22: 1843–52 (1978)). Since opioid antagonists do not exhibit binding that is sensitive to guanine nucleotides and sodium, this effect is used as a method for distinguishing agonists from antagonists using binding assays.

In addition, agonist activity can directly be assessed by the functional result within the cell. For example, it is known that the binding of opioid agonists inhibits cAMP formation, inhibits potassium channel activation, inhibits calcium channel activation, and stimulates GTPase. Assessment of these activities in response to a candidate compound is diagnostic of agonist activity. In addition, the ability of a compound to interfere with the activating activity of a known agonist such as etorphine effectively classifies it as an antagonist.

In one typical assay, the measurement of cAMP levels in cells expressing delta opioid receptors is carried out by determining the amount of $^3$H-cyclic AMP (cAMP) formed from intracellular ATP pools prelabeled with $^3$H-adenine. (Law, et al., *Mol. Pharmacol.*, 21:483–91 (1982)). Thus, cAMP formation assays are carried out with $0.5 \times 10^6$ cells/ 0.5 ml of $KRHB^2$ at pH 7.4, incubated at 37° C. for 20 minutes. After addition of the internal standard $^{32}$P-cyclic AMP, the radioactive cyclic AMP is separated from other $^3$H-labeled nucleotides by known double-column chromatographic methods. The opiate agonists' ability to inhibit cyclic AMP accumulation is then determined as described by Law, et al., *Mol. Pharmacol.*, 21:483–91 (1982).

The potency of a candidate opiate antagonist can be determined by measuring the ability of etorphine to inhibit cyclic AMP accumulation in the presence and in the absence of known amounts of these candidate antagonists. The inhibition constant ($K_i$) of an antagonist can then be calculated from the equation for competitive inhibitors.

An interesting feature of screening assays using the prior art NG108-15 cells is that the agonist adenylate cyclase inhibition function apparently does not require binding of all receptors on these cells. Thus, the inhibition constant and the dissociation constant for the opioid ligands differed for these cells.

The foregoing assays, as described above, performed on the recombinantly transformed cells of the invention, form a more direct and more convenient screen for candidate compounds having agonist and antagonist delta opioid receptor activity than that previously available in the art. Furthermore, such assays are more sensitive since cells can, in accordance with the present invention, be engineered to express high levels of the delta opioid receptor. Additionally, cells engineered in accordance with the present invention will circumvent the concern attendant to NG108-15 cells, that the cellular environment of that cancer hybrid artifactually effects the delta opioid receptor expressed thereon.

Methods to Prepare Delta Opioid Receptor Protein or Portions Thereof

The present invention provides the amino acid sequence of a murine delta opioid receptor; similarly, the availability of the cDNA of the invention places within possession of the art corresponding vertebrate opioid receptors whose amino acid sequence may also be determined by standard methods. As the amino acid sequences of such opioid receptors are known, or determinable, in addition to purification of such receptor protein from native sources, recombinant production or synthetic peptide methodology may also be employed.

The delta opioid receptor or portions thereof can thus also be prepared using standard solid phase (or solution phase) peptide synthesis methods, as is known in the art. In addition, the DNA encoding these peptides may be synthesized using commercially available oligonucleotide synthesis instrumentation for production of the protein in the manner set forth above. Production using solid phase peptide synthesis is, of course, required if non-gene-encoded amino acids are to be included.

The nomenclature used to describe the peptides and proteins of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $NH3^+$ and C-terminal $COO^-$ at physiological pH are understood to be present though not necessarily specified and shown, either in specific examples or in generic formulas. Free functional groups on the side chains of the amino acid residues may also be modified by glycosylation, phosphorylation, cysteine binding, amidation, acylation or other substitution, which can, for example, alter the physiological, biochemical, or biological properties of the compounds without affecting their activity within the meaning of the appended claims.

In the peptides shown, each gene-encoded residue, where appropriate, is represented by a single letter designation, corresponding to the trivial name of the amino acid, in accordance with the following conventional list:

| Amino Acid | One-Letter Symbol | Three-letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Nomenclature of Enkephalins

Enkephalins are either of two peptides of 5 residues with the N-terminal residue numbered 1:

```
tyr-gly-gly-phe-xxx (SEQ ID NO:4)
 1   2   3   4   5
```

In "met enkephalin" the 5th residue is methionine:

tyr-gly-gly-phe-met (SEQ ID NO: 5)

In "leu enkephalin" the 5th residue is leucine:

tyr-gly-gly-phe-leu (SEQ ID NO: 6)

Analogs can be made with (i) amino acid substitutions, (ii) D-amino acid substitutions, and/or (iii) additional amino acids. The site at which the substitution is made is noted at the beginning of the compound name. For example, "(D-ala$^2$, D-leu$^5$) enkephalin" means that D-ala is present at the second position and D-leu is present at the fifth position:

tyr-[D-ala]-gly-phe-[D-leu]

One letter abbreviations can also be used. Thus, "(D-ser$^2$) leu enkephalin" could be abbreviated as "DSLE." Additional residues are noted as well. Thus, the addition of a threonine residue (to the sixth position) of (D-ser$^2$) leu enkephalin would be "(D-ser$^2$) leu enkephalin thr" which could be abbreviated as "DSLET":

tyr-[D-ser]-gly-phe-leu-thr

Antibodies

Antibodies immunoreactive with critical positions of the delta opioid receptor can be obtained by immunization of suitable mammalian subjects with peptides, containing as antigenic regions those portions of the receptor intended to be targeted by the antibodies. Certain protein sequences have been determined to have a high antigenic potential. Such sequences are listed in antigenic indices, for example, MacVector software (I.B.I.). Thus, by determining the sequence of the delta opioid receptor protein then evaluating the sequence with an antigenic index probable antigenic sequences are located.

Antibodies are prepared by immunizing suitable mammalian hosts according to known immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended or interspersed with cysteine residues, for example, to facilitate linking to carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. The immortalized cell lines secreting the desired antibodies are screened by immunoassay in which the antigen is the peptide hapten or is the delta opioid receptor itself displayed on a recombinant host cell. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

Standard Methods

The techniques for sequencing, cloning and expressing DNA sequences encoding the amino acid sequences corresponding to a delta opioid receptor, e.g. polymerase chain reaction (PCR), synthesis of oligonucleotides, probing a cDNA library, transforming cells, constructing vectors, preparing antisense oligonucleotide sequences based on known sense nucleotide sequences, extracting messenger RNA, preparing cDNA libraries, and the like are well-established in the art. Skilled artisans are familiar with the standard resource materials for specific conditions and procedures. The following paragraphs are provided for convenience, it being understood that the invention is limited only by the appended claims.

RNA Preparation and Northern Blot

RNA preparation is as follows: The samples used for preparation of RNA are immediately frozen in liquid nitrogen and then stored until use at −80° C. The RNA is prepared by CsCl centrifugation (Ausubel et al., supra) using a modified homogenization buffer (Chirgwin et al., *Biochem.* 18:5294–5299 (1979)). Poly (A$^+$)RNA is selected by oligo (dT) chromatography (Aviv and Leder, *Proc. Natl. Acad. Sci. USA* 69:1408–1412 (1972)). RNA samples are stored at −80° C.

Analysis of gene expression and tissue distribution can be accomplished using Northern blots using, e.g., radiolabeled probes. The mRNA is size separated using gel electrophoresis and then typically is transferred to a nylon membrane or to nitrocellulose, and hybridized with radiolabeled probe. Presence of the hybridized probe is detected using autoradiography.

Cloning

The cDNA sequences encoding the delta opioid protein were obtained from a random-primed, size-selected cDNA library.

Alternatively, the cDNA sequences encoding delta opioid receptor protein are obtained from a cDNA library prepared from mRNA isolated from cells expressing the receptor protein in various organs such as the brain, according to procedures described in *Molecular Cloning: A Laboratory Manual,* Cold Spring Harbor, second edition, Sambrook, et al., eds. (1989).

The cDNA insert from the successful clone, excised with a restriction enzyme such as EcoRI, is then used as a probe of the original cDNA library or other libraries (low stringency) to obtain the additional clones containing inserts encoding other regions of the protein that together or alone span the entire sequence of nucleotides coding for the protein.

An additional procedure for obtaining cDNA sequences encoding the delta opioid receptor protein is PCR. PCR is used to amplify sequences from a pooled cDNA library of reversed-transcribed RNA, using oligonucleotide primers based on the transporter sequences already known.

Vector Construction

Construction of suitable vectors containing the desired coding and control sequences employs ligation and restriction techniques which are well understood in the art (Young et al., *Nature* 316:450–452 (1988)). Double-stranded cDNA encoding delta opioid receptor protein is synthesized and prepared for insertion into a plasmid vector CDM8. Alternatively, vectors such as Bluescript$^2$ or Lambda ZAP$^2$ (Stratagene, San Diego, Calif.) or a vector from Clontech, Palo Alto, Calif., can be used in accordance with standard procedures (see, e.g., *Molecular Cloning: A Laboratory Manual,* Cold Spring Harbor, Sambrook, et al., eds. second edition (1989)).

Site specific DNA cleavage is performed by treating with the suitable restriction enzyme, such as EcoRI (or enzymes), under conditions which are generally understood in the art, and the particulars of which are specified by the manufacturer of these commercially available restriction enzymes. See, e.g., New England Biolabs, Product Catalog. In general, about 1 μg of DNA is cleaved by one unit of enzyme in about 20 μl of buffer solution; in the examples herein, typically, an excess of restriction enzyme is used to ensure complete digestion of the DNA substrate. Incubation times of about one hour to two hours at about 37° C. are workable, although variations can be tolerated. After each incubation, protein is removed by extraction with phenol/chloroform, and can be followed by other extraction and the nucleic acid recovered from aqueous fractions by precipitation with ethanol.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of Na$^+$ and Mg$^{++}$ using about 1 unit of BAP or CIP per µg of vector at 60° C. or 37° C., respectively, for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

Ligations are performed in 15–50 µl volumes under the following standard conditions and temperatures: 20 mM Tris-HCl, pH 7.5, 10 mM MgCl$_2$, 10 mM DTT, 33 µg/ml BSA, 10 mM to 50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations (usually employing a 10–30 fold molar excess of linkers) are performed at 1 µM total ends concentration.

Correct ligations for vector construction are confirmed according to the procedures of Young et al., Nature, 316:450–452 (1988).

cDNA Library Screening cDNA libraries can be screened using reduced stringency conditions as described by Ausubel et al., Current Protocols in Molecular Biology, Greene Publishing and Wiley-Interscience, New York (1990), or by using methods described in *Molecular Cloning: A Laboratory Manual*, Cold Spring Harbor, Sambrook et al., eds., second edition (1989), or by using a colony or plaque hybridization procedure with a fragment of the DOR-1 cDNA coding for delta opioid receptor protein.

Plaque hybridization is typically carried out as follows: Host bacteria such as LE 392 (Stratagene) are grown overnight at 37° in LB Broth (*Molecular Cloning: A Laboratory Manual*, supra), gently pelleted and resuspended in one half the original volume of 10 mM MgSO$_4$, 10 mM CaCl$^2$. After titration, an amount of the phage library containing approximately 50,000 plaque forming units (pfu) is added to 300 µl of the host bacteria, incubated at 37° for 15 minutes and plated onto NZYCM agar with 10 ml NZYCM top agarose. A total of a million plaques distributed on 20 fifteen cm plates are screened. For colony screening, transfected bacteria are plated onto LB broth plates with the appropriate antibiotics. After the plaques or colonies have grown to 1 mm, the plates are chilled at 4° C. for at least two hours, and then overlaid with duplicate nitrocellulose filters, followed by denaturation of the filters in 0.5 M NaOH/1.5 M NaCl for five minutes and neutralization in 0.5 M Tris, pH 7.4/1.5 M NaCl for five minutes. The filters are then dried in air, baked at 80° C. for two hours, washed in 5X SSC/0.5% SDS at 68° C. for several hours, and prehybridized in 0.5 M NaPO$_4$, pH 7.2/1% BSA/1 mM EDTA/7% SDS/100 µg/ml denatured salmon sperm DNA for more than 4 hours. Using the DOR-1 cDNA (described herein) labeled by random priming as a probe, high stringency hybridization is carried out in the same solution at 68° C., and the temperature is reduced to 50–60° C. for lower stringency hybridization. After hybridization for 16–24 hours, the filters are washed first in 40 mM NaPO$_4$, pH 7.2/0.5% BSA/5% SDS/1 mM EDTA twice for one hour each, then in 40 mM NaPO$_4$, pH 7.2/1% BSA/1 mM EDTA for one hour each, both at the same temperature as the hybridization (Boulton et al., Cell 65:663–675 (1991)). The filters will then be exposed to film with an enhancing screen at −70° C. for one day to one week.

Positive signals are then aligned to the plates, and the corresponding positive phage is purified in subsequent rounds of screening, using the same conditions as in the primary screen. Purified phage clones are then used to prepare phage DNA for subcloning into a plasmid vector for sequence analysis. The various independent clones are also analyzed in terms of tissue distribution, using Northern blots and in situ hybridization using standard methods, as well as in terms of function, using expression in a heterologous eucaryotic expression system such as COS cells.

Expression of Delta Opioid Receptor Protein

The complete nucleotide sequence, described herein, encoding delta opioid receptor protein can be expressed in a variety of systems. The cDNA can be excised by suitable restriction enzymes and ligated into procaryotic or eucaryotic expression vectors for such expression.

For example, as set forth below, the cDNA encoding the protein is expressed in COS cells. To effect functional expression, the plasmid expression vector CDM8 (Aruffo and Seed, Proc. Natl. Acad. Sci. USA 84:8573–8577 (1987), provided by Drs. Aruffo and Seed (Harvard University, Boston, Mass.) was used. Alternatively, other suitable expression vectors such as retroviral vectors can be used.

Both procaryotic and eucaryotic systems can be used to express the delta opioid receptor; however, eucaryotic hosts are preferred.

Eucaryotic microbes, such as yeast, can be used as hosts for mass production of the delta opioid receptor protein. Laboratory strains of *Saccharomyces cerevisiae*, Baker's yeast, are used most, although a number of other strains are commonly available. Vectors employing, for example, the 2µ origin of replication of Broach, Meth. Enz. 101:307 (1983), or other yeast compatible origins of replications (see, e.g., Stinchcomb et al., Nature 282:39 (1979)); Tschempe et al., Gene 10:157 (1980); and Clarke et al., Meth. Enz. 101:300 (1983)) can be used. Control sequences for yeast vectors include promoters for the synthesis of glycolytic enzymes (Hess et al., J. Adv. Enzyme Reg. 7:149 (1968); Holland et al., Biochemistry 17:4900 (1978)). Additional promoters known in the art include the promoter for 3-phosphoglycerate kinase (Hitzeman et al., J. Biol. Chem. 255:2073 (1980)), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the coding sequences. Such terminators are found in the 3' untranslated region following the coding sequences in yeast-derived genes.

Alternatively, genes encoding delta opioid receptor protein are expressed in eucaryotic host cell cultures derived from multicellular organisms. (See, e.g., *Tissues Cultures*, Academic Press, Cruz and Patterson, eds. (1973)). These systems have the additional advantage of the ability to splice out introns, and thus can be used directly to express genomic fragments. Useful host cell lines include amphibian oocytes such as Xenopus oocytes, COS cells, VERO and HeLa cells, Chinese hamster ovary (CHO) cells, and insect cells such as SF9 cells. Expression vectors for such cells ordinarily include promoters and control sequences compatible with mammalian cells such as, for example, the commonly used early and late promoters from baculovirus, vaccinia virus, Simian Virus 40 (SV40) (Fiers et al., *Nature* 273:113 (1973)), or other viral promoters such as those derived from polyoma, Adenovirus 2, bovine papilloma virus, or avian sarcoma viruses. The controllable promoter, hMTII (Karin et al., *Nature* 299:797–802 (1982)) may also be used. General aspects of mammalian cell host system transformations have been described by Axel (U.S. Pat. No. 4,399,216 issued Aug. 16, 1983). It now appears, that "enhancer" regions are important in optimizing expression; these are, generally, sequences found upstream or downstream of the promoter region in non-coding DNA regions. Origins of replication can be obtained, if needed, from viral sources. However, integration into the chromosome is a common mechanism for DNA replication in eucaryotes.

If procaryotic systems are used, an intronless coding sequence should be used, along with suitable control sequences. The cDNA of delta opioid receptor protein can be excised using suitable restriction enzymes and ligated into procaryotic vectors along with suitable control sequences for such expression.

Procaryotes most frequently are represented by various strains of *E. coli;* however, other microbial strains may also be used. Commonly used procaryotic control sequences which are defined herein to include promoters for transcription initiation, optionally with an operator, along with ribosome binding site sequences, including such commonly used promoters as the beta-lactamase (penicillinase) and lactose (lac) promoter systems (Chang et al., *Nature* 198:1056 (1977)) and the tryptophan (trp) promoter system (Goeddel et al., *Nucleic Acids Res.* 8:4057 (1980)) and the lambda derived $P_L$ promoter and N-gene ribosome binding site (Shimatake et al., *Nature* 292:128 (1981)).

Depending on the host cell used, transformation is carried out using standard techniques appropriate to such cells. The treatment employing calcium chloride, as described by Cohen, *Proc. Natl. Acad. Sci. USA* (1972) 69:2110 (1972) or the $CaCl_2$ method described in Maniatis, et al., *Molecular Cloning: A Laboratory Manual,* Cold Spring Harbor Press, Sambrook et al., 2nd edition (1989)) can be used for procaryotes or other cells which contain substantial cell wall barriers. For mammalian cells without such cell walls, the calcium phosphate precipitation method of Graham and van der Eb, *Virology* 54:546 (1978), optionally as modified by Wigler et al., *Cell* 16:777–785 (1979), or by Chen and Okayama, supra, can be used. Transformations into yeast can be carried out according to the method of Van Solingen et al., *J. Bact.* 130:946 (1977), or of Hsiao et al., *Proc. Natl. Acad. Sci. USA* 76:3829 (1979).

Other representative transfection methods include viral transfection, DEAE-dextran mediated transfection techniques, lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

Modulation of Expression by Antisense Sequences

Alternatively, antisense sequences may be inserted into cells expressing delta opioid receptors as a means to modulate functional expression of the receptors encoded by sense oligonucleotides. The antisense sequences are prepared from known sense sequences (either DNA or RNA), by standard methods known in the art. Antisense sequences specific for the delta opioid receptor gene or RNA transcript can be used to bind to or inactivate the oligonucleotides encoding the delta opioid receptor.

Terminology

As used herein, the singular forms "a", "an" and "the" include plural reference unless the context clearly dictates otherwise. Thus, for example, reference to "a receptor" includes mixtures of such receptors, reference to "an opioid" includes a plurality of and/or mixtures of such opioids and reference to "the host cell" includes a plurality of such cells of the same or similar type and so forth.

Unless defined otherwise all technical and scientific terms used herein have the same meaning as commonly understood by one of ordinary skill in the art to which this invention belongs. The following examples are intended to illustrate but not to limit the invention. Temperatures are in ° C. and pressures at near atmospheric unless otherwise specified.

Preparation of Mono $^{125}$I-DADLE

DADLE (Peninsula Laboratories Inc.) was iodinated using the iodogen method. (Maidment, et al., in *Microdialysis in the Neurosciences,* T. Robinson and J. Justice, eds., pp. 275–303 (Elsevier, 1991)). Both mono- and di-iodinated forms are produced. It has been reported that di-iodo-DADLE does not bind opiate receptors, due to the di-iodination of the tyrosine residue. (Miller, R. J., et al., *Life Sci.* 22(5):379–88 (February 1978)). Accordingly, mono-iodinated DADLE is preferred. Mono-$^{125}$I-DADLE is also preferred because it has extremely high specific activity compared to DADLe labeled with other isotopes. Thus, exposure times on the order of days, rather than weeks or months can be used.

By employing a molar ratio of sodium iodide to peptide of approximately 1:100 when carrying out iodination, the yield of the preferred mono-iodinated DADLE was increased. Additionally, to further enhance the yield of the mono-iodinated form, iodinated DADLE (containing both mono- and di-iodinated forms) was purified by reverse-phase HPLC. (Maidment et al., supra) Employing this procedure a single major radiolabeled peak of the mono-iodinated DADLE separated from di-iodinated and non-iodinated forms.

DADLE monolabeled with 125I is crucial to successful screening. Radiolabeled $^{125}$I-DADLE differs from DADLE in several important parameters—size, hydrophobicity, and binding affinity (slightly lower). The purification of mono-iodinated from di-iodinated and non-iodinated DADLE by the HPLC step yields a ligand with very high specific activity (approximately 2000 Ci/mmol). The specific activity of the mono-iodinated form is approximately 100 times greater than that obtained by using the unseparated mixture of mono-, di-, and non-iodinated DADLE. Monolabeled $^{125}$I-DADLE must be used within a few days of its preparation.

EXAMPLE 1

Preparation of DOR-1

The NG108-15 cell line (available from Dr. Christopher Evans, U.C.L.A.) comprises a homogeneous and enriched source of delta opioid receptors. Utilizing mRNA isolated from NG108-15, a random-primed, size-selected cDNA library was constructed in plasmid vector CDM8. The cDNA library was amplified in bacteria. The cDNA library was transfected into COS-7 cells by electroporation. Transiently transfected COS lawns were screened and selected with highly purified mono-$^{125}$I2dAla, 5dLeu enkephalin ($^{125}$I-DADLE). Positive clones were identified by film autoradiography, and plasmids from these cells were recovered and amplified in bacteria. Thereafter, the plasmids were re-transfected into COS cells. Following three cycles of such plasmid enrichment, individual clones were transfected and a pure clone was identified that bound $^{125}$I-DADLE.

A. Construction of the cDNA Library

RNA was prepared from NG108-15 cells by homogenization in 6 M guanidinium isothiocyanate, followed by centrifugation through cesium chloride (J. M. Chirgwin, et al., *Biochemistry* 18:5294 (1979)). Poly-A$^+$ RNA was isolated by chromatography over oligo-dT-cellulose (H. Aviv and P. Leder, *Proc. Natl. Acad. Sci. USA* 69: 1408 (1972)). Using this RNA as a template, random hexamers were used to prime cDNA synthesis by avian myeloblastosis virus reverse transcriptase (Life Sciences Inc.). Second strand synthesis was accomplished with RNase-H and *E. coli* DNA polymerase (U. Gubler and B. J. Hoffman, *Gene* 24: 263 (1983)). The ends of the cDNAs were rendered blunt with T4 DNA polymerase and BstXI linkers were added. cDNA longer than 1.5 kB was selected by electrophoresis through 5% acrylamide followed by electro-elution. The 1.5 kB cDNA was ligated to the CDM8 vector (A. Aruffo and B. Seed, *Proc. Natl. Acad. Sci. USA* 84: 8573 (1987)), and then transformed into MC-1061 bacteria by electroporation (W. J. Dower, J. F. Miller and C. W. Ragsdale, *Nucl. Acids Res.* 16: 6127 (1988)). Accordingly, six pools of plasmid DNA were prepared from the original cDNA library of approximately 2×10$^6$ recombinants.

B. Plasmid Transfection by Electroporation and Expression in COS cells

COS cells were grown at high density and were harvested in trypsin, then resuspended at 2×10$^7$/ml in 1.2X RPMI containing 20% fetal calf serum. These cells were then incubated for ten minutes at 4° C. with 20 ug recombinant plasmid DNA from the cDNA library of paragraph A, and then electroporated at 960 uF and 230 V in a 0.4 cm gap cuvette (BioRad). The cells were then incubated an additional ten minutes at 4° C., and then plated into Dulbecco's Modified Eagle's Medium (DMEM) plus 10% fetal calf serum (FCS).

C. Screening of Transfected COS Cells

The transfected COS cells as obtained in paragraph B were grown for three days, then screened using radiolabeled mono $^{125}$I-DADLE. Transfected COS lawns were washed with PBS, then incubated at room temperature with 10–20 nM $^{125}$I-DADLE in KHRB containing 1% BSA. After 1 hour, the plates were washed rapidly several times with ice cold PBS then dried on ice with strong flow of forced cold air. Plates were exposed on Dupont Cronex film in cassettes at room temperature. Positive clones were identified by careful alignment of the film with the petri dish via low power microscopy.

DNA was removed from positive cells by solubilization in 0.1% SDS in TE containing 1 $\mu$g/$\mu$l tRNA delivered from a syringe attached to a capillary tube on a micromanipulator. Plasmids were purified from the extracted cells using the Hirt lysis procedure (Hirt, B., *J. Mol. Biol.* 26: 365–369 (1967)), and electroporated into MC-1061 bacteria. The plasmids were purified then retransfected into COS cells. Following three such enriching cycles, individual plasmid clones were transfected into COS cells yielding a single clone, named the DOR-1 clone.

EXAMPLE 2

Characterization of DOR-1

The DOR-1 clone initially was characterized by screening cell membrane fractions, from cells expressing DOR-1, with the labelled DADLE it was found that binding of $^{125}$I DADLE was displaced by nanomolar concentrations of opiate alkaloids diprenorphine, morphine, etorphine, and by DADLE, DSLET and DPDPE. Dextrophan (10 $\mu$M) did not displace the $^{125}$I DADLE, whereas its opioid-active enantiomer levorphanol did displace the radiolabeled DADLE (data not illustrated). Additionally, the $\mu$-selective ligand DAGO (5 $\mu$M) did not displace the counts (data not illustrated).

Figure 2:
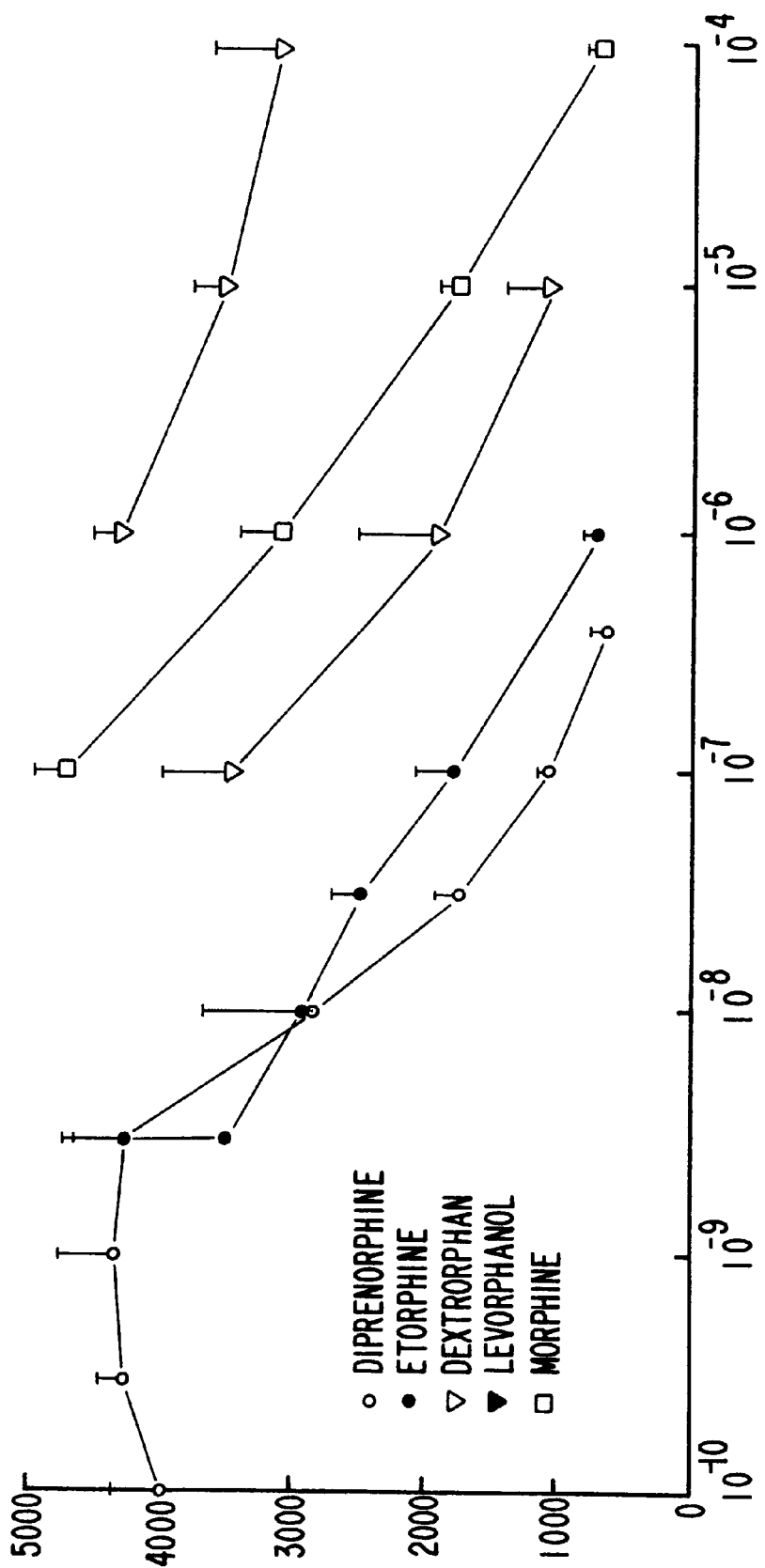
FIG. 2 depicts displacement curves of 5 nM 3H-Diprenorphine from COS cell membranes of cells transfected with DOR-1. The 3H-Diprenorphine was displaced by diprenorphine, etorphine, morphine and levorphanol, but not by dextrorphan, the non-opiate active optical isomer of levorphanol.
Figure 3:
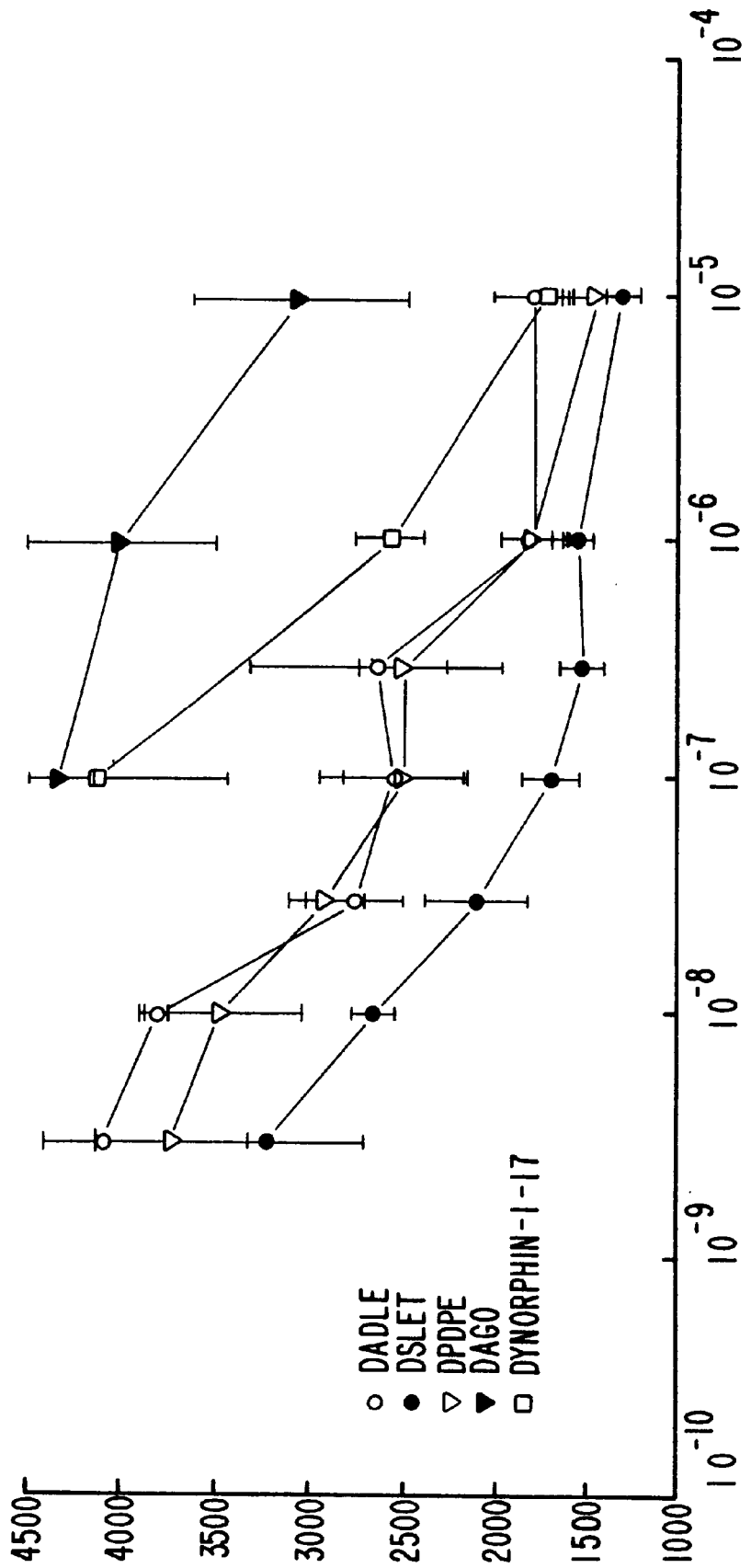
FIG. 3 depicts displacement curves of 5 nm 3H-Diprenorphine from COS cell membranes of cells transfected with DOR-1. The 3H-Diprenorphine was displaced by DPDPE and DSLET, delta-selective agonists; by DADLE, a high affinity ligand for mu and delta receptors; and by Dynorphin 1–17, a kappa-preferring ligand. It was not displaced by DAGO, a mu-selective ligand.

The DOR-1 clone was further characterized pharmacologically by assessing binding of $^3$H-diprenorphine to intact cells expressing the DOR-1 clone (FIG. 1), and by assessing displacement of $^3$H-diprenorphine from membrane fractions of such cells (FIGS. 2 and 3).

Binding assays were conducted on intact cells in KRHB, 1% BSA; or on membranes in 25 mM HEPES, 5 mM MgCl$_2$ pH 7.7. Cells were harvested with PBS containing 1 mM EDTA, washed 2× with PBS then resuspended in KHRB. Membranes prepared from the cells (Law P. Y. E, et al., *Mol. Pharm.* 23: 26–35 (1983)) were used directly in the binding assay. Binding assays were conducted in 96 well polypropylene cluster plates (Costar), at 4° C. in a total volume of 100 $\mu$l with an appropriate amount of radiolabeled ligand. Following 1 hour of incubation, plates were harvested on a Tomtec harvester and "B" type filtermats were counted in a Betaplate (Pharmacia) scintillation counter using Meltilex B/HS (Pharmacia) melt-on scintillator sheets.

Intact cells expressing DOR-1 were analyzed with the high affinity opiate antagonist $^3$H-diprenorphine. Specific binding was defined by the counts displaced by 400 nM Diprenorphine. FIG. 1 shows a saturation curve for $^3$H-diprenorphine for NG108-15 cells, and COS-7 cells transfected with the delta opioid receptor clone. Untransfected COS cells, or COS cells transfected with plasmid having no insert showed no specific binding. Thus, it was seen that the opioid binding of COS-DOR-1 cells is similar to that of NG108-15 cells.

Membranes prepared by standard methods from transfected COS-7 cells were employed for a more extensive pharmacological characterization of the receptor encoded by the DOR-1 clone. The affinities for the alkaloid opiates in competition for $^3$H-diprenorphine are illustrated in FIG. 2, and the affinities for the opioid peptides in competition for $^3$H-diprenorphine are set forth in FIG. 3.

The alkaloid opiates tested in FIG. 2 were unlabeled diprenorphine, a high affinity antagonist for delta receptors; etorphine, a high affinity agonist for delta, mu and kappa receptors; levorphanol, a low affinity agonist for delta receptors; morphine, a low affinity agonist for delta receptors and a high affinity agonist for mu receptors; and dextrorphan, a non-opiate active enantiomer of levorphanol which should not bind delta receptors. As shown in FIG. 2, the displacement of $^3$H-diprenorphine, in decreasing order of affinity, was observed with diprenorphine, etorphine, levorphanol and morphine. As expected, $^3$H-diprenorphine was not displaced by dextrorphan.

The opioid peptides tested in FIG. 3 were DADLE, a high affinity agonist for mu and delta receptors; DSLET and DPDPE, both high affinity agonists of delta (but not mu) receptors; DAGO, a selective agonist for mu receptors; and Dynorphin 1–17, a high affinity agonist for kappa receptors and moderate to low affinity agonist for delta receptors. As shown in FIG. 3, the displacement of $^3$H-diprenorphine, in decreasing order of affinity, was observed for DSLET, DPDPE and DADLE, and Dynorphin 1–17. Only weak displacement by DAGO was observed.

Thus, the rank order of the alkaloid opiate and opioid peptide affinities and selectivities for the cloned delta opioid receptor support the hypothesis that the DOR-1 clone encodes a delta opioid receptor.

EXAMPLE 3

Northern Blot Analysis of RNA

For Northern analysis, the mRNA from NG108-15 cells, and from cells dissected from regions of rat brain was separated by electrophoresis through 2.2 M formaldehyde/ 1.5% agarose, blotted to nylon and hybridized in aqueous solution at high stringency. The filters were prehybridized in 0.5 M NaPO$_4$, pH 7.2; 1% BSA; 1 mM EDTA; 7% SDS; and 100 ug/ml denatured salmon sperm DNA for at least four hours at 68° C. (T. G. Boulton et al., Cell 65: 663 (1991)). The filters were then hybridized overnight under these same conditions with ≧5×10$^6$ cpm/ml purified cDNA insert labelled by random priming (A. P. Feinberg and B. Vogelstein, Anal. Biochem. 132: 6 (1983)). The filters were twice washed in 40 mM NaPO$_4$, pH 7.2; 0.5% BSA; 5% SDS; and 1 mM EDTA for one hour, and then washed twice in 40 mM NaPO$_4$, pH 7.2; 1% SDS; and 1 mM EDTA for one hour each, all at 68° C. Thereafter autoradiography was performed with DuPont Cromex Lightening Plus at −70° C.

Figure 4:
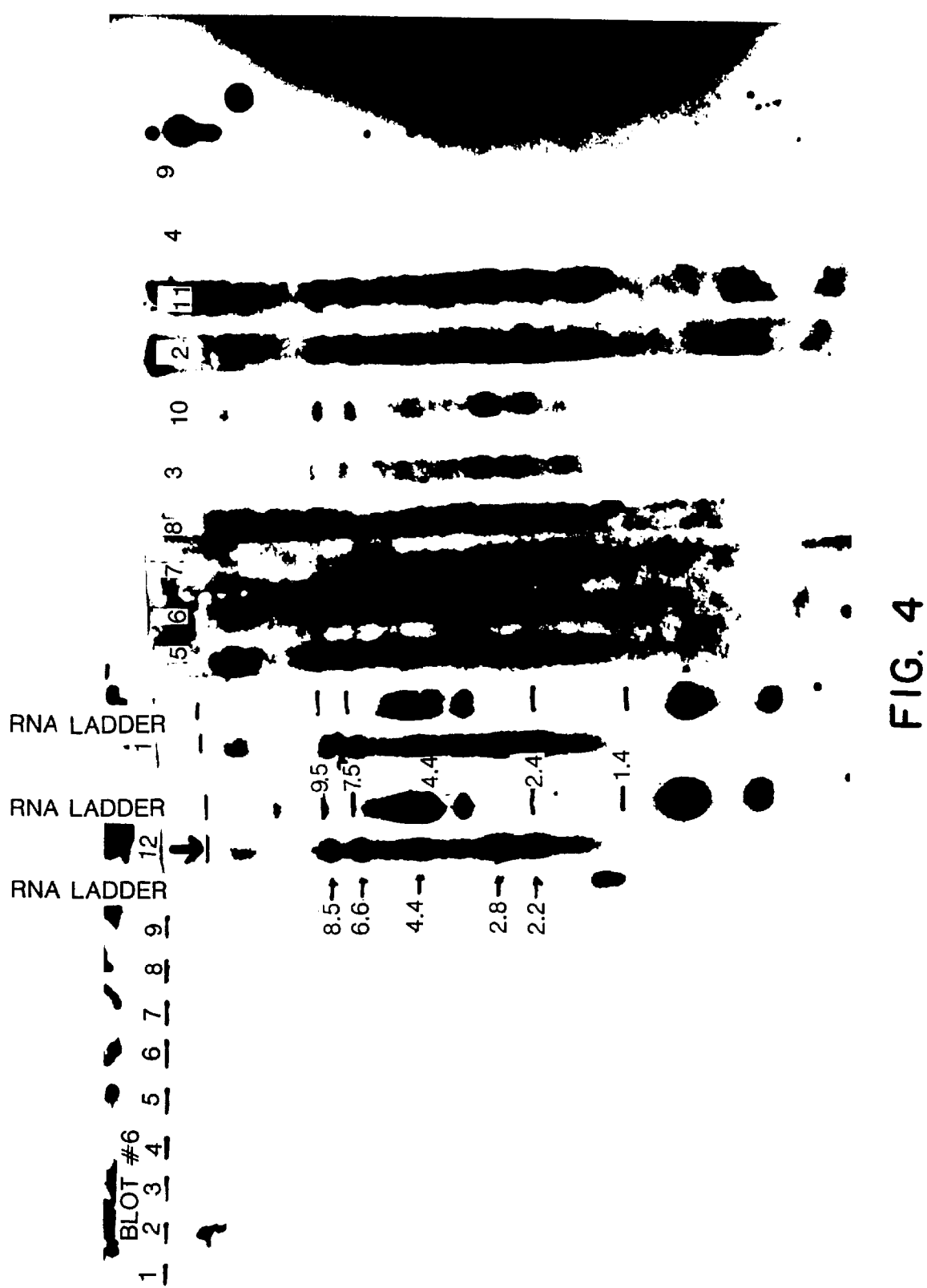
FIG. 4 depicts the results of a Northern Blot of mRNA from NG108-15 cells and cells from various rat brain regions.

The results of the Northern analysis of the mRNA showed the presence of multiple bands hybridizing to the probe at approximately 8.7, 6.8, 4.4, 2.75 and 2.2 kilobases (Kb) (FIG. 4). Also, the Northern analysis indicates that the pattern of mRNA may vary between brain regions. At present, it is unclear whether these mRNAs encode different protein sequences, and if so, whether these messages represent different types or sub-types of opioid receptors.

EXAMPLE 4

Southern Blot Analysis of DNA

Figure 7:
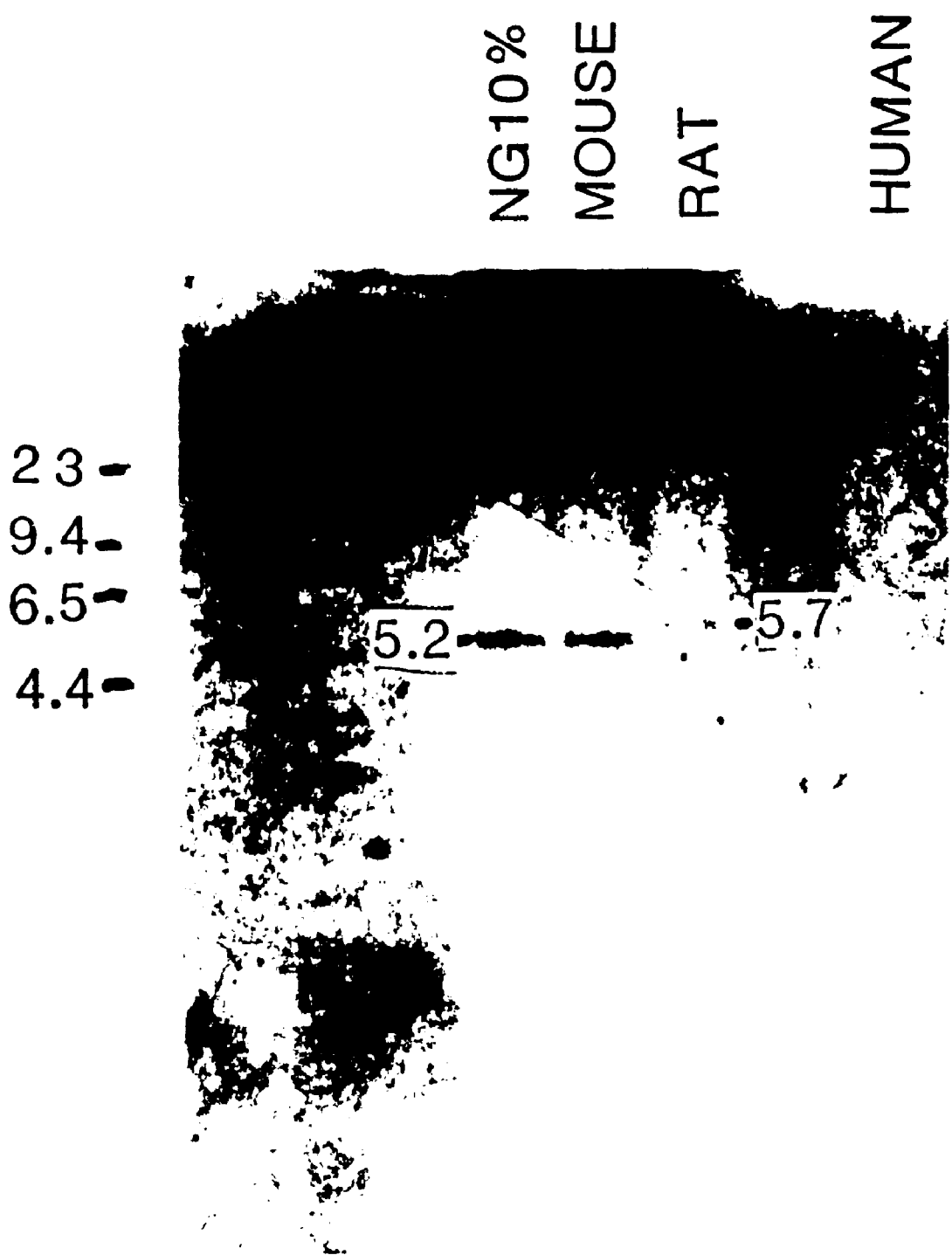
FIG. 7 depicts a Southern blot of radiolabeled DOR-1 cDNA probe hybridized at high stringency to NG108-15, mouse, rat and human DNA cut with BamHI.

The radiolabeled DOR-1 cDNA probe was hybridized to genomic Southern blots by standard methods. (Sambrook, supra) Accordingly, the radiolabeled DOR-1 cDNA probe was hybridized under high stringency conditions to a blot of NG108-15, mouse, rat and human DNA cut with restriction endonuclease Bam HI. (FIG. 7) Single bards were observed in the clones containing the NG108-15, mouse, and rat DNA. The sizes of the bands hybridizing to the cDNA probe estimated to be 5.2 kB (NG108-15), 5.2 kB (mouse), and 5.7 kB (rat). These data manifest the close homology of the mouse and rat genes, and also demonstrate that the DOR-1 clone is from the murine parent of the NG108-15 cell line.

In a blot containing EcoRI-cut genomic DNA from many different species (data not illustrated), hybridization of the DOR-1 cDNA under conditions of moderate stringency showed two bands in each lane of mouse, rat, human, rabbit, and several other mammalian species. This demonstrates that the opioid receptor gene in all of these species is closely related. Further, these data show that the genes or cDNAs from each of these species may readily be cloned using hybridization under moderate stringency.

EXAMPLE 5

Determination of the cDNA Sequence

Isolated cDNA encoding the delta opioid receptor was analyzed by subcloning the insert from the cDNA clone into a plasmid such as pBluescript™ (Stratagene, San Diego, Calif.) and using the dideoxy method (Sanger et al., Proc. Natl. Acad. Sci. USA 74:5463–5467 (1977)). The sequence of the cDNA was determined from single-stranded DNA and specifically designed internal primers, using both Sequenase and ΔTaq cycle sequencing kits (USB). These kits utilize the dideoxy chain termination method and are widely used in the art. The DNA sequence and predicted protein sequence was then compared to established databanks such as GenBank.

By sequencing the cDNA insert in the DOR-1 clone, an open reading frame of 370 amino acids was revealed. (FIG. 5) Comparisons with known sequences in GenBank showed highest homology between DOR-1 and the G-protein-coupled receptor for somatostatin (57% amino acid identity), and slightly lower homology with the receptor binding angiotensin, the two chemotactic factors IL-8 and N-formyl peptide. FIG. 6 shows the homology to the human somatostatin 1 receptor. The close homology of the present delta-receptor clone with the somatostatin receptor is especially noteworthy since somatostatin ligands are reported to bind to opioid receptors, and to have molecular mechanisms similar to those in delta receptors.

Other features of the DOR-1 clone deduced from the cDNA sequence include three consensus glycosylation sites at residues 18 and 33 (predicted to be in the extracellular N-terminal domain), and at residue 310 (close to the C-terminus and predicted to be intracellular). Phosphokinase C consensus sites are present within predicted intracellular domains, at residues 242, 255, 344, and 352. Seven putative membrane-spanning regions were identified based on hydrophobicity profiles, as well as homology with Rhodopsin and other G-protein coupled receptors which have been analyzed with respect to membrane-spanning regions using MacVector (I.B.I.) analysis. The DOR-1 clone isolated in accordance with the principles of the present invention produces a delta receptor with a predicted molecular weight of 40,558 daltons prior to post-translational modifications such as N-glycosylation.

EXAMPLE 6

Isolation of Opioid Receptor Genomic Clones

Genomic clone isolation was carried out according to techniques known in the art. To isolate opiate receptor genomic clones, 300,000 human genomic clones in γ gem 11 (Promega) and a similar number of mouse genomic clones in lambda Fix (Stratagene) were plated on host strain Le392 and probed with the 1.1 kB delta opiate receptor pst/xba 1 fragment, obtained by standard methods. It has been determined by standard methodology that the 1.1 Kb probe primarily contains coding region. The conditions for hybridization were of fairly low stringency-50% formamide/6XSSC, overnight at 37° C. The washes were performed also at low stringency-2X SSC, 0.1% SDS at room temperature.

One mouse clone and 4 human genomic clones were isolated and purified by sequential rounds of hybridization and plaque purification. DNA preparation and restriction analysis showed that the four human clones had very different Eco R1 digestion patterns. The 1.1 kB opiate receptor probe hybridized to a different single Eco R1 band in Southern blot analysis. (data not shown).

The genomic clones were digested into smaller fragments by Eco R1 and Taq 1, then shotgun cloned into the appropriate site of Bluescript. The sequence of these human genomic clones appears very similar to the original mouse cDNA, but some divergences are apparent. Such divergences are common within species, and often occur in regions that are not essential for function.

Accordingly, a human genomic clone has been isolated (DOR-h1) that encodes a delta opioid receptor. A partial sequence of Human Genomic Clone DOR-h1 reads:

-CAC TCT TGC ATT GCT CTA GGT TAC ACA (SEQ ID NO:7)

AAC AGC TGC CTC AAC CCA GTC CTT TAT

GCA TTT CTG GAT GAA AAC TTC AAA CGA

TGC TTC AGA-)

Seventy out of ninety nucleotides of the human DNA (DOR-h1) match exactly with DOR-1 DNA near the 3' end of the mouse cDNA.

When the amino acid sequence encoded by these DNA sequences are compared, it is found that there is 27 out of 30 amino acid identity:

EXAMPLE 7

Isolation of Delta Opioid Receptor Clones From Additional Organisms

In order to isolate the delta opioid receptor from mammalian brain cells, for example human brain cells, a random-primed human brainstem cDNA library in lambda Zap (Stratagene) was screened using the murine cDNA encoding the DOR-1 described herein. Positive plaques were purified and rescreened. Individual positive clones are sequenced and characterized as above.

EXAMPLE 8

Determination of Probable Antigenic Sequences

By evaluating the amino acid sequence of the DOR-1 delta opioid receptor with the MacVector (I.B.I.) antigenic index, and the antigenic index in accordance to Jameson, B. and H. Wolf, *Comput. Applic. in the Biosciences,* 4, 181–186 (1988), the following underlined sequences of the delta opioid receptor were determined to have a high antigenic potential:

```
                                             (SEQ ID NO:10)
NH2MELVPSARAELOSSPLVNLSDAFPSAFPSAGANASGSPGARSAS

SLALAIAITALYSAVCAVGLLGNVLVMFGIVRYTKLKTATNIYIFNL

ALADALATSTLPFQSAKYLMETWPFGELLCKAVLSIDYYNMFTSIFT

LTMMSVDRYIAVCHPVKALDFRTPAKAKLINICIWVLASGVGVPIMV

MAVTQPRDGAVVCMLQFPSPSWYWDTVTKICVFLFAFVVPILIITVC

YGLMLLRLRSVRLLSGSKEKDRSLRRITRMVLVVVGAFVVCWAPIHI

FVIVWTLVDINRRDPLVVAALHLCIALGYANSSLNPVLYAFLDENFK

RCFRQLCRTPCGRQEPGSLRRPRQATTRERVTACTPSDGPGGGAAA-

COOH.
```

The N-terminal sequence is extracellular, the other four sequences are predicted to be intracellular.

```
DOR-1:  H L C I A L G Y A N S S L N P V L Y A F L D E N F K R C F R (SEQ ID NO:8)
          | | | | | |   | |   | | | | | | | | | | | | | | | | |
DOR-h1: H F C I A L G Y T N S C L N P V L Y A F L D E N F K R C F R (SEQ ID NO:9)
```

We claim:

1. An isolated and purified nucleic acid molecule which comprises a nucleotide sequence encoding a mammalian delta opioid receptor, said nucleotide sequence selected from the group consisting of:

a) a nucleotide sequence encoding the amino acid sequence of SEQ ID NO: 2;
b) a nucleotide sequence encoding the amino acid sequence of SEQ ID NO: 10; and
c) a nucleotide sequence encoding the amino acid sequence encoded by a nucleotide sequence that hybridizes under conditions of low stringency with the complement of SEQ ID NO: 1.

2. A DNA molecule comprising the nucleotide sequence according to claim 1, wherein said nucleotide sequence is operably linked to a promoter.

3. A host cell comprising the DNA molecule of claim 2.

4. The host cell of claim 3 which is selected from the group consisting of yeast cells, mammalian cells, insect cells and bacteria.

5. The host cell of claim 4, which is a COS-7 cell.

6. A method of producing host cells that express a mammalian delta opioid receptor, which method comprises the steps of obtaining the DNA molecule of claim 2, transforming said DNA molecule into host cells, and isolating host cells that express the mammalian delta opioid receptor.

7. A host cell prepared by the method of claim 6.

8. The DNA molecule of claim 2 wherein said nucleotide sequence encodes the delta opioid receptor of SEQ ID NO: 2.

9. The nucleic acid molecule of claim 1 wherein the receptor is the human delta opioid receptor.

10. The nucleic acid molecule of claim 1 wherein said nucleotide sequence encodes the delta opioid receptor of SEQ ID NO: 2.

11. A method of obtaining an isolated DNA molecule which encodes a delta opioid receptor of a particular mammal, comprising the steps of constructing a genomic or cDNA library prepared from the mammal, probing said library with a probe comprising the nucleotide sequence of SEQ ID NO: 1 under low stringency conditions, isolating DNA molecules to which said probe hybridizes.

12. A nucleic acid molecule comprising a nucleotide sequence which is the complement of the nucleotide sequence of SEQ ID NO: 1.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 1829 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 29..1144

(xi) SEQUENCE DESCRIPTION: SEQ ID NO:1:

```
GCACGGTGGA GACGGACACG GCGGCGCC ATG GAG CTG GTG CCC TCT GCC CGT          52
                                Met Glu Leu Val Pro Ser Ala Arg
                                  1               5

GCG GAG CTG CAG TCC TCG CCC CTC GTC AAC CTC TCG GAC GCC TTT CCC         100
Ala Glu Leu Gln Ser Ser Pro Leu Val Asn Leu Ser Asp Ala Phe Pro
     10                  15                  20

AGC GCC TTC CCC AGC GCG GGC GCC AAT GCG TCG GGG TCG CCG GGA GCC         148
Ser Ala Phe Pro Ser Ala Gly Ala Asn Ala Ser Gly Ser Pro Gly Ala
 25                  30                  35                  40

CGT AGT GCC TCG TCC CTC GCC CTA GCC ATC GCC ATC ACC GCG CTC TAC         196
Arg Ser Ala Ser Ser Leu Ala Leu Ala Ile Ala Ile Thr Ala Leu Tyr
                 45                  50                  55

TCG GCT GTG TGC GCA GTG GGG CTT CTG GGC AAC TGT CTC GTC ATG TTT         244
Ser Ala Val Cys Ala Val Gly Leu Leu Gly Asn Cys Leu Val Met Phe
             60                  65                  70

GGC ATC GTC CGG TAC ACC AAA TTG AAG ACC GCC ACC AAC ATC TAC ATC         292
Gly Ile Val Arg Tyr Thr Lys Leu Lys Thr Ala Thr Asn Ile Tyr Ile
         75                  80                  85

TTC AAT CTG GCT TTG GCT GAT GCG CTG GCC ACC AGC ACG CTG CCC TTC         340
Phe Asn Leu Ala Leu Ala Asp Ala Leu Ala Thr Ser Thr Leu Pro Phe
     90                  95                 100

CAG AGC GCC AAG TAC TTG ATG GAA ACG TGG CCG TTT GGC GAG CTG CTG         388
Gln Ser Ala Lys Tyr Leu Met Glu Thr Trp Pro Phe Gly Glu Leu Leu
105                 110                 115                 120

TGC AAG GCT GTG CTC TCC ATT GAC TAC TAC AAC ATG TTC ACT AGC ATC         436
Cys Lys Ala Val Leu Ser Ile Asp Tyr Tyr Asn Met Phe Thr Ser Ile
                125                 130                 135

TTC ACC CTC ACC ATG ATG AGC GTG GAC CGC TAC ATT GCT GTC TGC CAT         484
Phe Thr Leu Thr Met Met Ser Val Asp Arg Tyr Ile Ala Val Cys His
            140                 145                 150

CCT GTC AAA GCC CTG GAC TTC CGG ACA CCA GCC AAG GCC AAG CTG ATC         532
Pro Val Lys Ala Leu Asp Phe Arg Thr Pro Ala Lys Ala Lys Leu Ile
        155                 160                 165

AAT ATA TGC ATC TGG GTC TTG GCT TCA GGT GTC GGG GTC CCC ATC ATG         580
Asn Ile Cys Ile Trp Val Leu Ala Ser Gly Val Gly Val Pro Ile Met
    170                 175                 180

GTC ATG GCA GTG ACC CAA CCC CGG GAT GGT GCA GTG GTA TGC ATG CTC         628
Val Met Ala Val Thr Gln Pro Arg Asp Gly Ala Val Val Cys Met Leu
185                 190                 195                 200

CAG TTC CCC AGT CCC AGC TGG TAC TGG GAC ACT GTG ACC AAG ATC TGC         676
Gln Phe Pro Ser Pro Ser Trp Tyr Trp Asp Thr Val Thr Lys Ile Cys
                205                 210                 215

GTG TTC CTC TTT GCC TTC GTG GTG CCG ATC CTC ATC ATC ACG GTG TGC         724
Val Phe Leu Phe Ala Phe Val Val Pro Ile Leu Ile Ile Thr Val Cys
```

```
                    220                  225                  230
TAT GGC CTC ATG CTA CTG CGC CTG CGC AGC GTG CGT CTG CTG TCC GGT        772
Tyr Gly Leu Met Leu Leu Arg Leu Arg Ser Val Arg Leu Leu Ser Gly
            235                  240                  245

TCC AAG GAG AAG GAC CGC AGC CTG CGG CGC ATC ACG CGC ATG GTG CTG        820
Ser Lys Glu Lys Asp Arg Ser Leu Arg Arg Ile Thr Arg Met Val Leu
        250                  255                  260

GTG GTG GTG GGC GCC TTC GTG GTG TGC TGG GCG CCC ATC CAC ATC TTC        868
Val Val Val Gly Ala Phe Val Val Cys Trp Ala Pro Ile His Ile Phe
265                  270                  275                  280

GTC ATC GTC TGG ACG CTG GTG GAC ATC AAT CGG CGC GAC CCA CTT GTG        916
Val Ile Val Trp Thr Leu Val Asp Ile Asn Arg Arg Asp Pro Leu Val
                285                  290                  295

GTG GCC GCA CTG CAC CTG TGC ATT GCG CTG GGC TAC GCC AAC AGC AGC        964
Val Ala Ala Leu His Leu Cys Ile Ala Leu Gly Tyr Ala Asn Ser Ser
            300                  305                  310

CTC AAC CCG GTT CTC TAC GCC TTC CTG GAC GAG AAC TTC AAG CGC TGC       1012
Leu Asn Pro Val Leu Tyr Ala Phe Leu Asp Glu Asn Phe Lys Arg Cys
        315                  320                  325

TTC CGC CAG CTC TGT CGC ACG CCC TGC GGC CGC CAA GAA CCC GGC AGT       1060
Phe Arg Gln Leu Cys Arg Thr Pro Cys Gly Arg Gln Glu Pro Gly Ser
330                  335                  340

CTC CGT CGT CCC CGC CAG GCC ACC ACG CGT GAG CGT GTC ACT GCC TGC       1108
Leu Arg Arg Pro Arg Gln Ala Thr Thr Arg Glu Arg Val Thr Ala Cys
345                  350                  355                  360

ACC CCC TCC GAC GGC CCG GGC GGT GGC GCT GCC GCC TGACCTACCC            1154
Thr Pro Ser Asp Gly Pro Gly Gly Gly Ala Ala Ala
                365                  370

GACCTTCCCC TTAAACGCCC CTCCCAAGTG AAGTGATCAG AGGCCACACC GAGCTCCCTG     1214

GGAGGCTGTG GCCACCACCA GGACAGCTAG AATTGGGCCT GCACAGAGGG GAGGCCTCCT     1274

GTGGGGACGG GCCTGAGGGA TCAAAGGCTC CAGGTTGGAA CGGTGGGGGT GAGGAAGCAG     1334

AGCTGGTGAT TCCTAAACTG TATCCATTAG TAAGGCCTCT CAATGGGACA GAGCCTCCGC     1394

CTTGAGATAA CATCGGGTTC TGGCCTTTTT GAACACCCAG CTCCAGTCCA AGACCCAAGG     1454

ATTCCAGCTC CAGAACCAGG AGGGGCAGTG ATGGGGTCGA TGATTTGGTT TGGCTGAGAG     1514

TCCCAGCATT TGTGTTATGG GGAGGATCTC TCATCTTAGA GAAGAAAGGG GACAGGGCAT     1574

TCAGGCAAGG CAGCTTGGGG TTTGGTCAGG AGATAAGCGC CCCCCTTCCC TTGGGGGGAG     1634

GATAAGTGGG GGATGGTCAC GTTGGAGAAG AGTCAAAGTT CTCACCACCT TTCTAACTAC     1694

TCAGCTAAAC TCGTTGAGGC TAGGGCCAAC GTGACTTCTC TGTAGAGAGG TACAAGCCGG     1754

GCCTGATGGG GCAGGCCTGT GTAATCCCAG TCATAGTGGA GGCTGAGGCT GGAAAATTAA     1814

GGACCAACAG CCCGG                                                     1829

(2) INFORMATION FOR SEQ ID NO:2:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Leu Val Pro Ser Ala Arg Ala Glu Leu Gln Ser Ser Pro Leu
  1               5                  10                  15

Val Asn Leu Ser Asp Ala Phe Pro Ser Ala Phe Pro Ser Ala Gly Ala
                20                  25                  30
```

Asn Ala Ser Gly Ser Pro Gly Ala Arg Ser Ala Ser Ser Leu Ala Leu
            35                  40                  45

Ala Ile Ala Ile Thr Ala Leu Tyr Ser Ala Val Cys Ala Val Gly Leu
    50                  55                  60

Leu Gly Asn Cys Leu Val Met Phe Gly Ile Val Arg Tyr Thr Lys Leu
65                  70                  75                  80

Lys Thr Ala Thr Asn Ile Tyr Ile Phe Asn Leu Ala Leu Ala Asp Ala
                85                  90                  95

Leu Ala Thr Ser Thr Leu Pro Phe Gln Ser Ala Lys Tyr Leu Met Glu
            100                 105                 110

Thr Trp Pro Phe Gly Glu Leu Leu Cys Lys Ala Val Leu Ser Ile Asp
        115                 120                 125

Tyr Tyr Asn Met Phe Thr Ser Ile Phe Thr Leu Thr Met Met Ser Val
    130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Asn Ile Cys Ile Trp Val Leu Ala
                165                 170                 175

Ser Gly Val Gly Val Pro Ile Met Val Met Ala Val Thr Gln Pro Arg
            180                 185                 190

Asp Gly Ala Val Val Cys Met Leu Gln Phe Pro Ser Pro Ser Trp Tyr
        195                 200                 205

Trp Asp Thr Val Thr Lys Ile Cys Val Phe Leu Phe Ala Phe Val Val
    210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
                245                 250                 255

Arg Arg Ile Thr Arg Met Val Leu Val Val Gly Ala Phe Val Val
            260                 265                 270

Cys Trp Ala Pro Ile His Ile Phe Val Ile Val Trp Thr Leu Val Asp
        275                 280                 285

Ile Asn Arg Arg Asp Pro Leu Val Val Ala Ala Leu His Leu Cys Ile
    290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Thr Pro
                325                 330                 335

Cys Gly Arg Gln Glu Pro Gly Ser Leu Arg Arg Pro Arg Gln Ala Thr
            340                 345                 350

Thr Arg Glu Arg Val Thr Ala Cys Thr Pro Ser Asp Gly Pro Gly Gly
        355                 360                 365

Gly Ala Ala Ala
        370

(2) INFORMATION FOR SEQ ID NO:3:

(i) SEQUENCE CHARACTERISTICS:
        (A) LENGTH: 369 amino acids
        (B) TYPE: amino acid
        (C) STRANDEDNESS: single
        (D) TOPOLOGY: linear (xi) SEQUENCE DESCRIPTION: SEQ ID NO:3:

Met Glu Leu Thr Ser Glu Gln Phe Asn Gly Ser Gln Val Trp Ile Pro
1               5                   10                  15

-continued

```
Ser Pro Phe Asp Leu Asn Gly Ser Leu Gly Pro Ser Asn Gly Ser Asn
            20                  25                  30

Gln Thr Glu Pro Tyr Tyr Asp Met Thr Ser Asn Ala Val Leu Thr Phe
        35                  40                  45

Ile Tyr Phe Val Val Cys Val Val Gly Leu Cys Gly Asn Thr Leu Val
50                      55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
                100                 105                 110

Ala Ile Cys Arg Val Val Met Thr Val Asp Gly Ile Asn Gln Phe Thr
                115                 120                 125

Ser Ile Phe Cys Leu Thr Val Met Ser Ile Asp Arg Tyr Leu Ala Val
                130                 135                 140

Val His Pro Ile Lys Ser Ala Lys Trp Arg Arg Pro Arg Thr Ala Lys
145                 150                 155                 160

Met Ile Asn Val Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
                180                 185                 190

Cys Thr Ile Asn Trp Pro Gly Glu Ser Gly Ala Trp Tyr Thr Gly Phe
                195                 200                 205

Ile Ile Tyr Ala Phe Ile Leu Gly Phe Leu Val Pro Leu Thr Ile Ile
                210                 215                 220

Cys Leu Cys Tyr Leu Phe Ile Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
                260                 265                 270

Tyr Ile Phe Asn Val Ser Ser Val Ser Val Ala Ile Ser Pro Thr Pro
                275                 280                 285

Ala Leu Lys Gly Met Phe Asp Phe Val Val Ile Leu Thr Tyr Ala Asn
                290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Ala Glu
                325                 330                 335

Asp Gly Glu Arg Ser Asp Ser Lys Gln Asp Lys Ser Arg Leu Asn Glu
                340                 345                 350

Thr Thr Glu Thr Gln Arg Thr Leu Leu Asn Gly Asp Leu Gln Thr Ser
                355                 360                 365

Ile
```

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:4:

Tyr Gly Gly Phe Xaa (2) INFORMATION FOR SEQ ID NO:5:

(i) SEQUENCE CHARACTERISTICS:
　　　　　(A) LENGTH: 5 amino acids
　　　　　(B) TYPE: amino acid
　　　　　(C) STRANDEDNESS: single
　　　　　(D) TOPOLOGY: linear (xi) SEQUENCE DESCRIPTION: SEQ ID NO:5:

Tyr Gly Gly Phe Met
1               5

(2) INFORMATION FOR SEQ ID NO:6:

(i) SEQUENCE CHARACTERISTICS:
　　　　　(A) LENGTH: 5 amino acids
　　　　　(B) TYPE: amino acid
　　　　　(C) STRANDEDNESS: single
　　　　　(D) TOPOLOGY: linear (xi) SEQUENCE DESCRIPTION: SEQ ID NO:6:

Tyr Gly Gly Phe Leu
1               5

(2) INFORMATION FOR SEQ ID NO:7:

(i) SEQUENCE CHARACTERISTICS:
　　　　　(A) LENGTH: 90 base pairs
　　　　　(B) TYPE: nucleic acid
　　　　　(C) STRANDEDNESS: single
　　　　　(D) TOPOLOGY: linear (xi) SEQUENCE DESCRIPTION: SEQ ID NO:7:

CACTCTTGCA TTGCTCTAGG TTACACAAAC AGCTGCCTCA ACCCAGTCCT TTATGCATTT    60

CTGGATGAAA ACTTCAAACG ATGCTTCAGA                                    90

(2) INFORMATION FOR SEQ ID NO:8:

(i) SEQUENCE CHARACTERISTICS:
　　　　　(A) LENGTH: 30 amino acids
　　　　　(B) TYPE: amino acid
　　　　　(C) STRANDEDNESS: single
　　　　　(D) TOPOLOGY: linear (xi) SEQUENCE DESCRIPTION: SEQ ID NO:8:

His Leu Cys Ile Ala Leu Gly Tyr Ala Asn Ser Ser Leu Asn Pro Val
1               5                  10                  15

Leu Tyr Ala Phe Leu Asp Glu Asn Phe Lys Arg Cys Phe Arg
            20                  25                  30

(2) INFORMATION FOR SEQ ID NO:9:

(i) SEQUENCE CHARACTERISTICS:
　　　　　(A) LENGTH: 30 amino acids
　　　　　(B) TYPE: amino acid
　　　　　(C) STRANDEDNESS: single
　　　　　(D) TOPOLOGY: linear (xi) SEQUENCE DESCRIPTION: SEQ ID NO:9:

His Phe Cys Ile Ala Leu Gly Tyr Thr Asn Ser Cys Leu Asn Pro Val
1               5                  10                  15

Leu Tyr Ala Phe Leu Asp Glu Asn Phe Lys Arg Cys Phe Arg
            20                  25                  30

(2) INFORMATION FOR SEQ ID NO:10:

(i) SEQUENCE CHARACTERISTICS:
        (A) LENGTH: 372 amino acids
        (B) TYPE: amino acid
        (C) STRANDEDNESS: single
        (D) TOPOLOGY: linear (xi) SEQUENCE DESCRIPTION: SEQ ID NO:10:

```
Met Glu Leu Val Pro Ser Ala Arg Ala Glu Leu Gln Ser Ser Pro Leu
 1               5                  10                  15

Val Asn Leu Ser Asp Ala Phe Pro Ser Ala Phe Pro Ser Ala Gly Ala
                20                  25                  30

Asn Ala Ser Gly Ser Pro Gly Ala Arg Ser Ala Ser Ser Leu Ala Leu
            35                  40                  45

Ala Ile Ala Ile Thr Ala Leu Tyr Ser Ala Val Cys Ala Val Gly Leu
50                  55                  60

Leu Gly Asn Val Leu Val Met Phe Gly Ile Val Arg Tyr Thr Lys Leu
65                  70                  75                  80

Lys Thr Ala Thr Asn Ile Tyr Ile Phe Asn Leu Ala Leu Ala Asp Ala
                85                  90                  95

Leu Ala Thr Ser Thr Leu Pro Phe Gln Ser Ala Lys Tyr Leu Met Glu
            100                 105                 110

Thr Trp Pro Phe Gly Glu Leu Leu Cys Lys Ala Val Leu Ser Ile Asp
            115                 120                 125

Tyr Tyr Asn Met Phe Thr Ser Ile Phe Thr Leu Thr Met Met Ser Val
130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Asn Ile Cys Ile Trp Val Leu Ala
                165                 170                 175

Ser Gly Val Gly Val Pro Ile Met Val Met Ala Val Thr Gln Pro Arg
            180                 185                 190

Asp Gly Ala Val Val Cys Met Leu Gln Phe Pro Ser Pro Ser Trp Tyr
            195                 200                 205

Trp Asp Thr Val Thr Lys Ile Cys Val Phe Leu Phe Ala Phe Val Val
210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
                245                 250                 255

Arg Arg Ile Thr Arg Met Val Leu Val Val Gly Ala Phe Val Val
            260                 265                 270

Cys Trp Ala Pro Ile His Ile Phe Val Ile Val Trp Thr Leu Val Asp
            275                 280                 285

Ile Asn Arg Arg Asp Pro Leu Val Val Ala Ala Leu His Leu Cys Ile
290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Thr Pro
                325                 330                 335

Cys Gly Arg Gln Glu Pro Gly Ser Leu Arg Arg Pro Arg Gln Ala Thr
            340                 345                 350

Thr Arg Glu Arg Val Thr Ala Cys Thr Pro Ser Asp Gly Pro Gly Gly
            355                 360                 365

Gly Ala Ala Ala
```

370

(2) INFORMATION FOR SEQ ID NO:11:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:11:

Met Glu Leu Val Pro Ser Ala Arg Ala Glu Leu Gln Ser Ser Pro
1            5                   10               15

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:12:

Cys His Pro Val Lys Ala Leu Asp Phe Arg Thr Pro Ala Lys Ala Lys
1            5                   10               15

Leu Ile Asn Ile
          20

(2) INFORMATION FOR SEQ ID NO:13:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:13:

Leu Leu Ser Gly Ser Lys Glu Lys Asp Arg Ser Leu Arg Arg Ile Thr
1            5                   10               15

(2) INFORMATION FOR SEQ ID NO:14:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:14:

Cys Gly Arg Gln Glu Pro Gly Ser Leu Arg Arg Pro Arg Gln Ala Thr
1            5                   10               15

(2) INFORMATION FOR SEQ ID NO:15:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:15:

Cys Thr Pro Ser Asp Gly Pro Gly Gly Gly Ala Ala Ala
1            5                   10